United States Patent
Barthelemy et al.

(10) Patent No.: US 10,633,408 B2
(45) Date of Patent: Apr. 28, 2020

(54) NUCLEOSIDE-LIPID COMPOUNDS WITH pH-SENSITIVE DIALKYLORTHOESTER CHAINS AND THEIR USE FOR TRANSPORTATION OR VECTORIZATION OF AT LEAST ONE THERAPEUTIC AGENT

(71) Applicants: UNIVERSITE DE BORDEAUX, Bordeaux (FR); INSTITUT NATIONAL DE LA SANTE ET DE LA RECHERCHE MEDICALE (INSERM), Paris (FR)

(72) Inventors: Philippe Barthelemy, Merignac (FR); Khalid Oumzil, Merignac (FR)

(73) Assignees: UNIVERSITE DE BORDEAUX, Bordeaux (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 15/575,857

(22) PCT Filed: May 19, 2016

(86) PCT No.: PCT/EP2016/061335
§ 371 (c)(1),
(2) Date: Nov. 21, 2017

(87) PCT Pub. No.: WO2016/188868
PCT Pub. Date: Dec. 1, 2016

(65) Prior Publication Data
US 2018/0118775 A1    May 3, 2018

(30) Foreign Application Priority Data
May 22, 2015 (EP) .................... 15305778

(51) Int. Cl.
C07H 19/06 (2006.01)
C07H 19/10 (2006.01)
(Continued)

(52) U.S. Cl.
CPC .......... *C07H 19/06* (2013.01); *A61K 9/1272* (2013.01); *A61P 35/00* (2018.01); *C07H 19/073* (2013.01);
(Continued)

(58) Field of Classification Search
CPC ..................................... C07H 19/06
See application file for complete search history.

(56) References Cited

U.S. PATENT DOCUMENTS 6,897,196 B1    5/2005 Szoka, Jr.

FOREIGN PATENT DOCUMENTS

WO    0220510 A1    3/2002
WO    2005116043 A1    12/2005

OTHER PUBLICATIONS

Wang P.,"Synthesis of phospholipid-inhibitor conjugates by enzymic transphosphatidylation with phospholipase D", Journal of the American Chemical Society, pp. 10487-10491, vol. 115, No. 23 (Nov. 1993).

*Primary Examiner* — Benjamin J Packard
(74) *Attorney, Agent, or Firm* — Browdy and Neimark, PLLC

(57) ABSTRACT

The invention relates to new nucleoside-lipid compounds with pH-sensitive dialkylorthoester chains, to the process for their preparation and to their uses, in particular their use for transportation or vectorization of at least one therapeutic agent.

17 Claims, 9 Drawing Sheets

(a) Na, overnight, 55°C, 55%
(b) MsCl, pyridine, overnight, RT, 62%
(c) 2, *tert*-butyldimethylsilylpentadione, PPTS, CH$_2$Cl$_2$, 4h, reflux, 94%
(d) NMe$_3$, THF, CH$_3$CN, 48 h, 90%

(51) Int. Cl.
  *C07H 19/073* (2006.01)
  *A61P 35/00* (2006.01)
  *A61K 9/127* (2006.01)
  *C12N 15/113* (2010.01)
(52) U.S. Cl.
  CPC ......... *C07H 19/10* (2013.01); *C12N 15/1137* (2013.01); *C12N 2310/14* (2013.01); *C12N 2320/32* (2013.01)

(e) TBDMSCl, imidazole, DMF, overnight, RT, 82%;
(f) 2, *tert*-butyldimethylsilylpentadione, PPTS, $CH_2Cl_2$, 4h, reflux, 83%,
(g) TBAF, THF, 1 h, RT, 94%
(h) 2-Cyanoethyl *N,N*- diisopropylchlorophosphoramidite, $iPr_2EtN$, $CH_2Cl_2$, 1 h, RT, 93%
(i) 1) 0.45 M tetrazole in acetonitrile, THF, $CH_3OH$, RT, 1 h; 2) 0.02 M $I_2$ in pyidine/H20/THF, RT, 5 h; 3) $Et_3N/CH_2Cl_2$: 9/1, overnight, 65%

NUCLEOSIDE-LIPID COMPOUNDS WITH PH-SENSITIVE DIALKYLORTHOESTER CHAINS AND THEIR USE FOR TRANSPORTATION OR VECTORIZATION OF AT LEAST ONE THERAPEUTIC AGENT

The invention relates to new nucleoside-lipid compounds with pH-sensitive dialkylorthoester chains, to the process for their preparation and to their uses, in particular their use for transportation or vectorization of at least one therapeutic agent.

The site-specific release via a programmed release of therapeutics is emerging as a promising approach to address the drug-delivery issue.

Among the various existing stimuli-responsive options, the micro-environmentally pH-sensitive delivery systems have been widely studied for biomedical applications. Indeed, the changes in the external pH can be exploited by pH-responsive systems, such as liposomes or vesicles, which respond to pH changes by displaying altered physicochemical properties, ensuring the triggered release of the drug in an acidic environment.

WO02/20510 relates to acid-sensitive compounds comprising a cyclic orthoester which is acid-sensitive and at least one hydrophilic substituent selected from polyalkylenes glycols, mono- or polysaccharides, hydrophilic therapeutic molecules or polyamine-type radicals. These compounds are able to form conjugates (liposomes, complexes, nanoparticles, etc.) with biologically active substances and release them in cell tissues or compartments where the pH is acid, either as non-ionic surfactant which stabilize the particles which encapsulate a biologically active substance and then destabilize them in an acid medium, or as a vector covalently bound to a therapeutic molecule so as to release said therapeutic molecule in cell tissues or compartments where the pH is acid. The orthoester linkage joins a hydrophilic part and a hydrophobic part. Upon degradation, there is no formation of a single-chain compound from a double-chain compound.

As stated in the paragraph bridging pages 3 and 4, these acid-sensitive compounds are particularly interesting because their sensitivity to pH can be modulated by the choice of the substituent of the central carbon atom and of the size of the orthoester cycle. Also, their degradation in acidic medium is "autocatalytic" as their partial degradation releases an acid, such as formic acid or acetic acid which lower the pH, thus further favoring the degradation of the the acid-sensitive compounds.

U.S. Pat. No. 6,897,196 relates to amphipathic lipid derivatives which degrade at acid pH, and to lipidic delivery systems containing them. These amphipathic lipid derivatives comprise a hydrophilic head group joined to a hydrophobic group by an acid-labile double orthoester linkage. After hydrolysis, these compounds form pentaerythritol, on the one hand, and hydrophilic and hydrophobic compounds coming from the head and tail, on the other hand.

It has now been found that new nucleoside-lipid (also called "nucleolipid" or "nucleolipidic") compounds with pH-sensitive dialkylorthoester chains can be used for preparing stabilized structures for encapsulating therapeutic agents, but also for destabilizing said structures in acid medium, on the one hand, and for destabilizing the cell endosomal membrane in which release of the therapeutic agent is desired, on the other hand.

This membrane destabilization occurs by interaction with the phospholipids which are present in the endosomal membrane.

This surprising property of membrane destabilization increases the intracellular release of the therapeutic agent.

Without wishing to be bound by theory, it can be hypothesized that this property may be related to the way how the nucleolipidic compound behaves when hydrolyzed. After hydrolysis in acid medium, the dialkylorthoester chain is cleaved into a single chain fatty alcohol and a nucleoside. The single chain fatty alcohol is able to bind to the cell endosomal membrane, whereby the destabilization of the membrane lipid bilayer is promoted.

However, the desired stability properties of the nucleoside-lipid compounds according to the invention result from a specific balance between the polar head derived from nucleotide and nucleoside moieties of the nucleolipid and the hydrophobic orthoester tail.

«Acid medium» is understood as a medium having a pH of about 4 to about 6.5, which is near the endosomal pH.

Contrary to the acid-sensitive compounds of WO02/20510, the invention does not aim at obtaining compounds which degrade all the more that pH decreases, because the invention aims at providing compounds which are able to dissociate at the endosomal pH. In prior studies, the inventors found that when using cyclic orthoesters as a substituent of the sugar residue of the nucleoside moiety, the compounds were not hydrolyzed in acidic conditions (pH=3), even after a period of several days. They were thus unable to be cleaved into a single chain fatty alcohol and a nucleoside, and thus to promote the destabilization of the membrane lipid bilayer and achieve the desired goal.

The invention thus relates to a compound of formula (I)

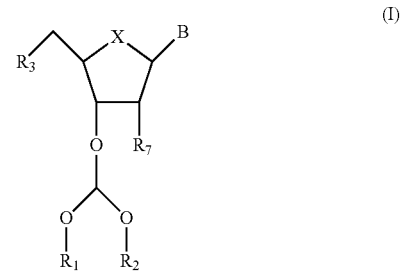

In which

X is an oxygen atom, a sulfur atom or a methylene group,

B is a purine or pyrimidine base, or their derivatives, or else a non-natural mono- or bi-cyclic heterocyclic base in which each cycle has 4 to 7 members, unsubstituted or substituted;

$R_1$ and $R_2$, identical or different, represent a straight or branched $C_2$-$C_{30}$ hydrocarbon chain, which is saturated or partially unsaturated, unsubstituted or substituted by at least one straight or branched, unsubstituted or substituted, $C_1$-$C_6$ alkyl group, and said straight or branched $C_2$-$C_{30}$ hydrocarbon chain being optionally partially halogenated, $R_3$ is a hydroxy, amino, phosphate, phosphonate, phosphatidylcholine, O-alkyl phosphatidylcholine, phosphocholine, O-alkyl phosphocholine, thiophosphate, phosphonium, sulfonate, silyl or phosphoramidite group, said groups being unsubstituted or substituted by at least one straight or branched, unsubstituted or substituted, $C_1$-$C_6$ alkyl group, or, when $R_3$ is a phosphate group, said group being unsubstituted or substituted by at least one straight or branched, unsubstituted or substituted, $C_1$-$C_{18}$ hydrocarbon chain, a $NH_2$—$R_4$, $NHR_4R_5$ or $NR_4R_5R_6$ group in which $R_4$, $R_5$ and $R_6$, identical or different, represent a hydrogen atom or a straight or branched $C_1$-$C_6$ alkyl group, or a $C_1$-$C_6$ straight or branched hydroxyalkyl group, where said alkyl or hydroxyalkyl groups are unsubstituted or substituted by at least one straight or branched, unsubstituted or substituted, $C_1$-$C_6$ alkyl group, or else a straight or branched $C_2$-$C_{30}$ hydrocarbon chain, which is unsubstituted or substituted by a hydroxyl group, or an heteroaryl group having 1 to 4 nitrogen atoms, which is unsubstituted or substituted by a straight or branched, unsubstituted or substituted, $C_2$-$C_{30}$ hydrocarbon chain or by a $(CH_2)_m$—O—$(CH_2)_p$—$R_9$ group in which m=1 to 6 and p=0 to 10 et $R_9$ represents a cyclic ketal group comprising 5 to 7 carbon atoms, which is unsubstituted or substituted by a straight or branched, unsubstituted or substituted, $C_2$-$C_{30}$ hydrocarbon chain, or by a sterol residue; or a —O—C(O)—$(CH_2)_q$—C(O)—O [$(CH_2)_2$—O]$_r$—H group in which q is 2 to 6 and r is an integer from 4 to 30, preferably from 10 to 20;

$R_7$ is hydrogen, a straight or branched, unsubstituted or substituted, $C_1$-$C_6$ alkyl group, a trifluoroalkyl, a halogen or a $C_1$-$C_6$ alkoxy group.

Preferably, X is an oxygen atom.

By «straight or branched $C_1$-$C_6$ alkyl group» is understood, for example, a methyl, ethyl, propyl, i-propyl, n-butyl, i-butyl, tert-butyl, preferably methyl or ethyl. Optionally, the straight or branched $C_1$-$C_6$ alkyl group may be substituted by at least one substituent selected from, for instance, a hydroxy, an amino, a $C_1$-$C_6$ alkoxy, a cyano, a nitro, or a carboxy group or a halogen atom, in particular a fluorine atom.

Preferred $C_2$-$C_{30}$ hydrocarbon chains are $C_8$-$C_{26}$, more preferably $C_{16}$-$C_{20}$ hydrocarbon chains.

Preferred straight or branched $C_2$-$C_{30}$ hydrocarbon chains are $C_8$-$C_{26}$, more preferably $C_{16}$-$C_{20}$ straight or branched hydrocarbon chains.

Preferred straight or branched $C_1$-$C_{18}$ hydrocarbon chains are $C_{14}$-$C_{18}$ more preferably $C_{18}$ straight or branched hydrocarbon chains.

The purine or pyrimidine base can be, for example, selected from, adenine, guanine, cytosine, xanthine, hypoxanthine, uric acid, caffeine, theobromine, uracile, thymine, dihydrouridine, and their derivatives.

Thymine and uracile are preferred.

Also, in formula (I) above, the purine or pyrimidine base can be substituted by at least one substituent selected from, for example, a halogen, an amino group, a carboxy group, a carbonyl group, a carbonylamino group, a hydroxy, azido, cyano, thiol, a $C_1$-$C_6$ straight or branched alkyl, cycloalkyl, perfluoroalkyl, alkyloxy (for example, methoxy), oxycarbonyl, vinyl, ethynyl, propynyl, acyl group etc.

By "derivatives of a purine or pyrimidine base" is meant, for example, a non-natural mono- or bi-cyclic heterocyclic base in which each cycle has 4 to 7 members, optionally substituted as stated above for the purine or pyrimidine base.

By «non-natural heterocyclic base» is meant a universal base, such as, for example, 3-nitropyrrole, 4-nitroimidazole or 5-nitroindole, which do not exist in nature.

By «heteroaryl comprising 1 to 4 nitrogen atoms» is meant a mono- or bi-cyclic carbocyclic group, aromatic or partially unsaturated, comprising 5 to 12 atoms, interrupted by 1 to 4 nitrogen atoms, which can be, for example, selected from furane, pyrrole, oxazole, oxadiazole, isoxazole, pyrazole, triazole, tetrazole, imidazole, pyridine, pyrimidine, pyridazine, pyrazine, benzofurane, indole, quinoleine, iso-quinoleine, chromane, naphtyridine and benzodiazine groups, triazole being preferred.

"Halogen atom" means fluorine, iodine, chlorine or bromine, fluorine being preferred.

«Hydrocarbon chain, which is partially halogenated» refers to a saturated or unsaturated alkyl chain in which some hydrogen atoms are replaced by halogen atoms, such as fluorine, iodine, chlorine or bromine, fluorine being preferred.

The following compounds of formula (I), in which at least one condition is fulfilled, are preferred:

X is an oxygen atom;

B is thymine, and $R_1$ and $R_2$ are identical and represent a straight or branched $C_2$-$C_{30}$ hydrocarbon chain, preferably $C_8$-$C_{26}$, more preferably $C_{16}$-$C_{20}$ hydrocarbon chain, which is saturated or partially unsaturated.

In particular, $R_1$ and $R_2$ are identical and represent a straight and saturated $C_{16}$-$C_{20}$ hydrocarbon chain.

Particularly preferred compounds of formula (I) are those in which:

X represents oxygen,

B is thymine, $R_1$ and $R_2$ are identical and represent a straight or branched $C_2$-$C_{30}$ hydrocarbon chain, preferably $C_8$-$C_{26}$, more preferably $C_{16}$-$C_{20}$ hydrocarbon chain, which is saturated or partially unsaturated, $R_3$ is:

a hydroxy group;

a $NR_4R_5R_6$ group, in which $R_4$, $R_5$ and $R_6$, identical or different, represent a hydrogen atom, or a $C_1$-$C_6$ straight or branched alkyl chain;

a trialkylamino group, in which the alkyl group is a $C_1$-$C_6$ straight or branched alkyl chain, in particular a trimethylamino group;

a phosphate or phosphonate group, which is unsubstituted or substituted by at least one straight or branched, unsubstituted or substituted, $C_1$-$C_6$ alkyl group; a sulfonate group, which is unsubstituted or substituted by at least one straight or branched, unsubstituted or substituted, $C_1$-$C_6$ alkyl group;

a trialkylphoshonium group which is unsubstituted or substituted by at least one straight or branched, unsubstituted or substituted, $C_1$-$C_6$ alkyl group;

a silyl group, which is unsubstituted or substituted by at least one straight or branched, unsubstituted or substituted, $C_1$-$C_6$ alkyl group;

a phosphoramidite group, which is unsubstituted or substituted by at least one straight or branched, unsubstituted or substituted, $C_1$-$C_6$ alkyl group, or else -O—C(O)—$(CH_2)_q$—C(O)—O [$(CH_2)_2$—O]$_r$—H in which q=2 and r is an integer from 4 to 30, preferably from 10 to 20.

In particular, $R_1$ and $R_2$ are identical and represent a straight and saturated $C_{16}$-$C_{20}$ hydrocarbon chain.

In particular, $R_3$ is a $NR_4R_5R_6$ group, in which $R_4$, $R_5$ and $R_6$, identical or different, represent a $C_1$-$C_6$ straight or branched alkyl chain, preferably a trimethylamino group; or a phosphate or phosphonate group, which is unsubstituted or substituted by at least one straight or branched, unsubstituted or substituted, $C_1$-$C_6$ alkyl group.

When $R_3$ is an anionic group, the counter-ion can be selected from those usual in the field, such as, for example $Et_3NH^+$, $Na^+$, $K^+$, $Li^+$, $NH_4^+$, $Ca^{2+}$, $Mg^{2+}$, $Fe^{2+}$, etc When $R_3$ is a cationic group, the counter-ion can be selected from those usual in the field, such as, for example $CH_3SO_3^-$, $CH_3C_6H_4SO_3^-$ ($TsO^-$), $I^-$, $Cl^-$, $Br^-$, etc.

Of particular interest are the compounds of formula (I) which are selected from:
((2R,3S,5R)-3-(bis(hexadecyloxy)methoxy)-5-(5-methyl-2,4-dioxo-3,4-dihydropyrimidin-1 (2H)-yl)tetrahydrofuran-2-yl)methyl methanesulfonate,
1-((2R,3S,5R)-3-(bis(hexadecyloxy)methoxy)-5-(5-methyl-2,4-dioxo-3,4-dihydropyrimidin-1 (2H)-yl)tetrahydrofuran-2-yl)-N,N,N-trimethyl-methanaminium methanesulfonate,
1-((2R,4S,5R)-4-(bis(hexadecyloxy)methoxy)-5-(((tert-butyldimethylsilyl)oxy)methyl)tetrahydrofuran-2-yl)-5-methylpyrimidine-2,4(1H,3H)-dione,
1-((2R,4S,5R)-4-(bis(hexadecyloxy)methoxy)-5-(hydroxymethyl)-tetrahydrofuran-2-yl)-5-methylpyrimidine-2,4(1H,3H)-dione,
((2R,3S,5R)-3-(bis(hexadecyloxy)methoxy)-5-(5-methyl-2,4-dioxo-3,4-dihydropyrimidin-1 (2H)-yl)tetrahydrofuran-2-yl)methyl (2-cyanoethyl) diisopropylphosphoramidite,
((2R,3S,5R)-3-(bis(hexadecyloxy)methoxy)-5-(5-methyl-2,4-dioxo-3,4-dihydropyrimidin-1(2H)-yl)tetrahydrofuran-2-yl)methyl methyl phosphate, and
((2R,3S,5R)-3-(bis(hexadecyloxy)methoxy)-5-(5-methyl-2,4-dioxo-3,4-dihydropyrimidin-1 (2H)-yl)tetrahydrofuran-2-yl)methyl O-Methyl-O'-succinyl-polyethyleneglycol 500.

The invention also relates to a process for preparing compounds of formula (I) which bear a $R_3$ cationic group, which comprises the following steps:
reacting a 5' hydroxyl nucleosyl compound of formula (III)

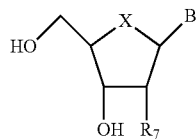

(III)

in which B and $R_7$ are as defined above for formula (I),
with an electrophilic reagent, to provide compounds of formula IV

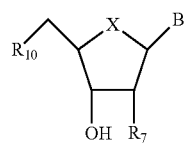

(IV)

where $R_{10}$ represents $R_3$ or $R_{10}$ is either a hydroxyl protecting group or a hydroxy activating moiety,
and, when $R_{10}$ is a hydroxyl protecting group, reacting the compound of formula (IV) with an orthoformate compound of formula (II)

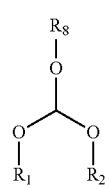

(II)

in which $R_1$, $R_2$ and $R_8$, identical, represent a straight or branched $C_2$-$C_{30}$ hydrocarbon chain, which is saturated or partially unsaturated, unsubstituted or substituted by at least one straight or branched, unsubstituted or substituted, $C_1$-$C_6$ alkyl group, and said straight or branched $C_2$-$C_{30}$, hydrocarbon chain being optionally partially or totally fluorinated, and
recovering the resulting compound of formula (V) thus obtained,

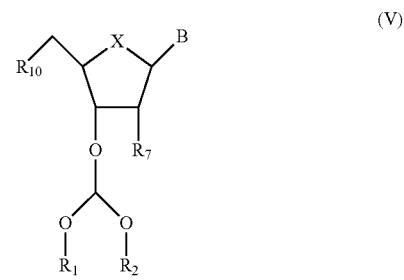

(V)

or, alternatively
when $R_{10}$ is a hydroxyl protecting group, deprotecting the resulting compound of formula (V) to obtain a compound bearing a hydroxyl group instead of $R_{10}$, and reacting the resulting compound with one or more appropriate reactants to obtain a compound of formula (I) bearing a $R_3$ substituent, or
when $R_{10}$ is hydroxy activating moiety, reacting the resulting compound of formula (V) with a nucleophile reagent to obtain a compound of formula (I) bearing a $R_3$ substituent.

Electrophilic reagents are known in the field and can be selected, for instance, from, allyl halides, benzyl halides, tert-butyl halides, trityl halides, for example trityl chloride (Trt-Cl), monomethoxytrityl chloride (MMT-Cl), dimethoxytrityl chloride (DMT-Cl), etc. or else, silyl chlorides, such as, for example, tert-butyldimethylsilyl chloride (TBDMS-Cl), etc., dinitrophenyl halides, such as dinitrophenyl chloride; acyl halides, such as acyl chlorides, methanesulfonate halide, such as mesyl chloride; paratolueneslfonate halides, such as tosyl-Cl; halogens; trifluoromethanesulfonate halides, such as triflate chloride etc.

By "hydroxyl protecting group" is meant a functional group which is introduced to mask the reactivity of the hydroxyl group. Suitable hydroxyl protecting groups can be, for instance, selected from ethers such as allyl ethers, benzyl ethers, tert-butyl ethers, trityl ethers such as for example, trityl ether, monomethoxytrityl ether, dimethoxytrityl ether, methyltrityl ether, ethyltrityl ether, methyltriphenylmethyl ether, etc; silyl ethers such as, for example, trimethyltylsilyl ether (TMS), triisopropylsylil ether (TIPS), tert-butyldimethylsilyl ether (TBDMS), tert-butyldpihenylsilyl ether (TBDPS), dinitrophenyl ether, acyl groups, etc.

For example, $R_{10}$ moieties of compounds (V) can be deprotected by using the adapted conditions known in the field, such as, for example by using tetra-n-butylammonium fluoride (for silyl ethers), light (for dinitrophenyl ethers), hydrogenolysis, etc. to provide compounds of formula (I) bearing the desired $R_3$ substituent.

Alternatively, according to the invention, selected hydroxyl protecting groups, such as for example tert-butyldimethylsilyl, can constitute the $R_3$ substituent, and thus be part of the final compounds of formula (I).

By "hydroxyl activating moiety" is meant a group which activates the hydroxyl towards a nucleophile attack, such as, for example, methanesulfonate (mesylate), paratoluenesulfonate (tosylate), halogen, trifluoromethanesulfonate (triflate) etc.

Nucleophilic reagents are known in the field and can be selected, for instance, among:

- amines, such as ammonia, $NH_2$—$R_4$, $NHR_4R_5$ or $NR_4R_5R_6$ group in which $R_4$, $R_5$ and $R_6$, identical or different, represent a hydrogen atom or a straight or branched, $C_1$-$C_6$ alkyl group, or a $C_1$-$C_6$ straight or branched hydroxyalkyl group, where said alkyl or hydroxyalkyl groups are unsubstituted or substituted by at least one straight or branched, unsubstituted or substituted, $C_1$-$C_6$ alkyl group or else a straight or branched $C_2$-$C_{30}$ hydrocarbon chain,
- oxygen nucleophiles, such as water; alcohols of formula R—OH, where R is preferably a $C_1$-$C_6$ straight or branched alkyl group; alkoxide anions of formula R—$O^-$, where R is as defined above, hydrogen peroxide and carboxylate anions of formula R'—$COO^-$, where R' is preferably a $C_2$-$C_{30}$ hydrocarbon chains,
- sulfur nucleophiles, such as thiols, thiolate anions, thiocarboxylate anions, dithiocarbonates anions and dithiocarbamates, and
- azide and alkyl azide.

The invention also relates to a compound of formula (I) for use as an agent for transportation, vectorization or cellular delivery of at least one therapeutic agent. Alternatively, the invention relates to an agent for transportation, vectorization or cellular delivery of at least one therapeutic agent which comprises a compound of formula (I).

Indeed, the compounds of formula (I) are able to form, in an aqueous medium, supramolecular structures, such as for example, liposomes, micelles or nanoparticles, which can include the therapeutic agent.

Liposomes can be, for instance, prepared by drying the compounds of formula (I) under dry $N_2$ and desiccating under vacuum. Liposomes are obtained after addition of an appropriate solvent to the dried nucleolipids to obtain liposomes dispersions, followed by Vortex agitation and sonication.

The invention thus relates to liposomes formed from at least one compound of formula (I) as defined above, optionally in association with a co-lipid.

The invention also relates to complexes formed from at least one compound of formula (I) as defined above in association with a co-lipid.

Such co-lipid can be, for example, selected from phosphatidylcholine derivatives, such as, for example, dioleylphosphatidylcholine (DOPC), dioleylphosphatidyluridine phosphatidylcholine (DOUPC), 1,2-dioléyl-sn-glycéro-3-phosphatidyléthanolamine (DOPE) or N-[5'-(2',3'-dioleoyl) uridine]-N',N',N'-trimethylammonium tosylate (DOTAU).

The invention further relates to compositions containing at least one compound of formula (I).

In particular, the invention concerns pharmaceutical compositions containing at least one compound of formula (I), at least one therapeutic agent and a pharmaceutically acceptable carrier.

By «therapeutic agent» is meant, for example, a natural or synthetic molecule used for preventing or treating a pathological condition, or restoring a biological function, in vitro or in vivo, in particular in animal, in particular in human beings, or else in isolated cells.

Preferably, when contained in a liposome formed from at least one compound of formula (I) as defined above, the therapeutic agent will be used at a concentration of about of 0.1 ng/mL to 10 mg/mL.

Advantageously, said therapeutic agent can be selected, for example, from anti-tumoral agents, antibiotic agents, anti-microbial agents, analgesic agents, ant-histaminic agents, bronchodilators agents, agents which are active on the central nervous system, anti-hypertension agents or agents which are active on the cardiovascular system (in particular vasodilator agents, anti-atherosclerosis agents such as agents having a platelet anti-aggregating activity); hormones, nucleic acids and their fragments; peptides, oligopeptides, proteins, antigens, antibodies or else stem cells etc.

The invention is illustrated non-limitatively by the examples below.

The examples entitled "Preparation" describe the preparation of synthesis intermediates used for preparing the compounds of formula (I). The preparation of the compounds of formula (I) and their applications are then described as "Examples".

All commercially available reagents and solvents (Fluka, Sigma-Aldrich, Alfa-Aesar) were used without further purification.

For reactions requiring anhydrous conditions, dry solvents were used (Sigma-Aldrich) under inert atmosphere (nitrogen or argon).

Column chromatography was performed with flash silica gel (0.04-0.063 mm, Merck) or LH20 size exclusion column (Sephadex® LH-20, Sigma Aldrich). All compounds were characterized using $^1H$ and $^{13}C$ Nuclear Magnetic Resonance (NMR) spectroscopy (Bruker Avance DPX-300 spectrometer, $^1H$ at 300.13 MHz and $^{13}C$ at 75.46 MHz). Assignments were made by $^1H$-$^1H$ COSY, DEPT and HSQC experiments. Chemical shifts (δ) are given in parts per million (ppm) relatively to tetramethylsilane or residual solvent peaks ($CHCl_3$: $^1H$: 7.26, $^{13}C$: 77.0). Coupling constants J are given in Hertz (Hz); peak multiplicity is reported as follows: s=singlet, bs=broad singlet, d=doublet, t=triplet, m=multiplet.

Zeta potential measurements and Dynamic light scattering (DLS) measurements of liposomes were performed with a MalvernNanoZS device.

The following abbreviations are used:
DCM dichloromethane
DMAB dimethylaminoborane
DMF dimethylformamide
DMSO dimethylsulfoxide
DOPC dioleylphosphatidylcholine
DOPE 1,2-dioleyl-sn-glycero-3-phosphatidylethanolamine
DOTAU N-[5'-(2',3'-dioleoyl)uridine]-N',N',N'-trimethylammonium tosylate
TEA triethylamine
THF tetrahydrofuran
TBDMS tert-Butyldimethylsilyl
TBDMSCI tert-Butyldimethylsilyl chloride FIG. 1 shows the synthetic scheme used for Preparations 1 and 2 and examples 1 and 2 (compounds of formula (I) bearing a cationic group at $R_3$).

Figure 10:
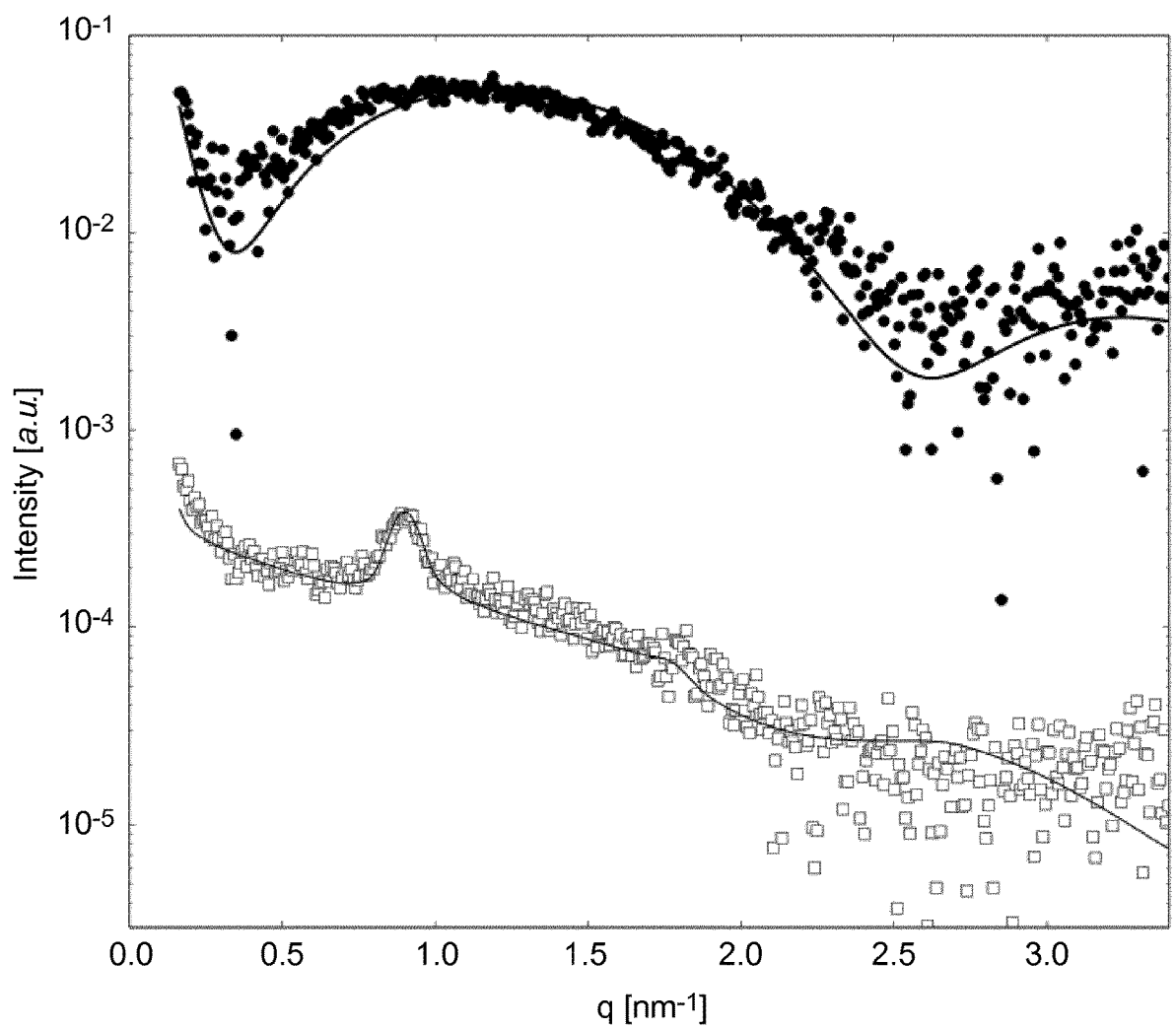

FIG. 10 shows the Small-Angle X-ray Scattering (SAXS) profile of compound 6/DOPC (mol ratio 50/50) before (•) and after (□) incubation at pH=5 and 37° C.

PREPARATION 1

Compound 2 tris(hexadecyloxy)methane

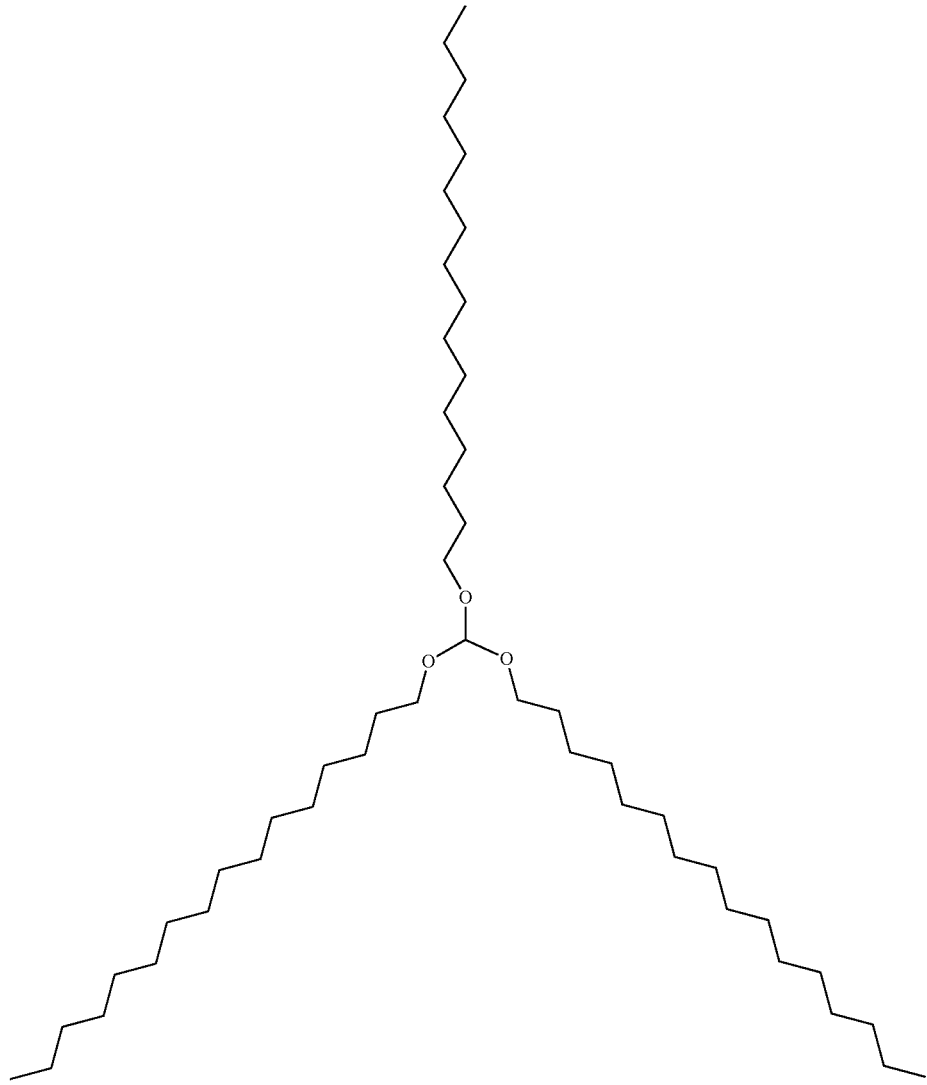

Figure 1:
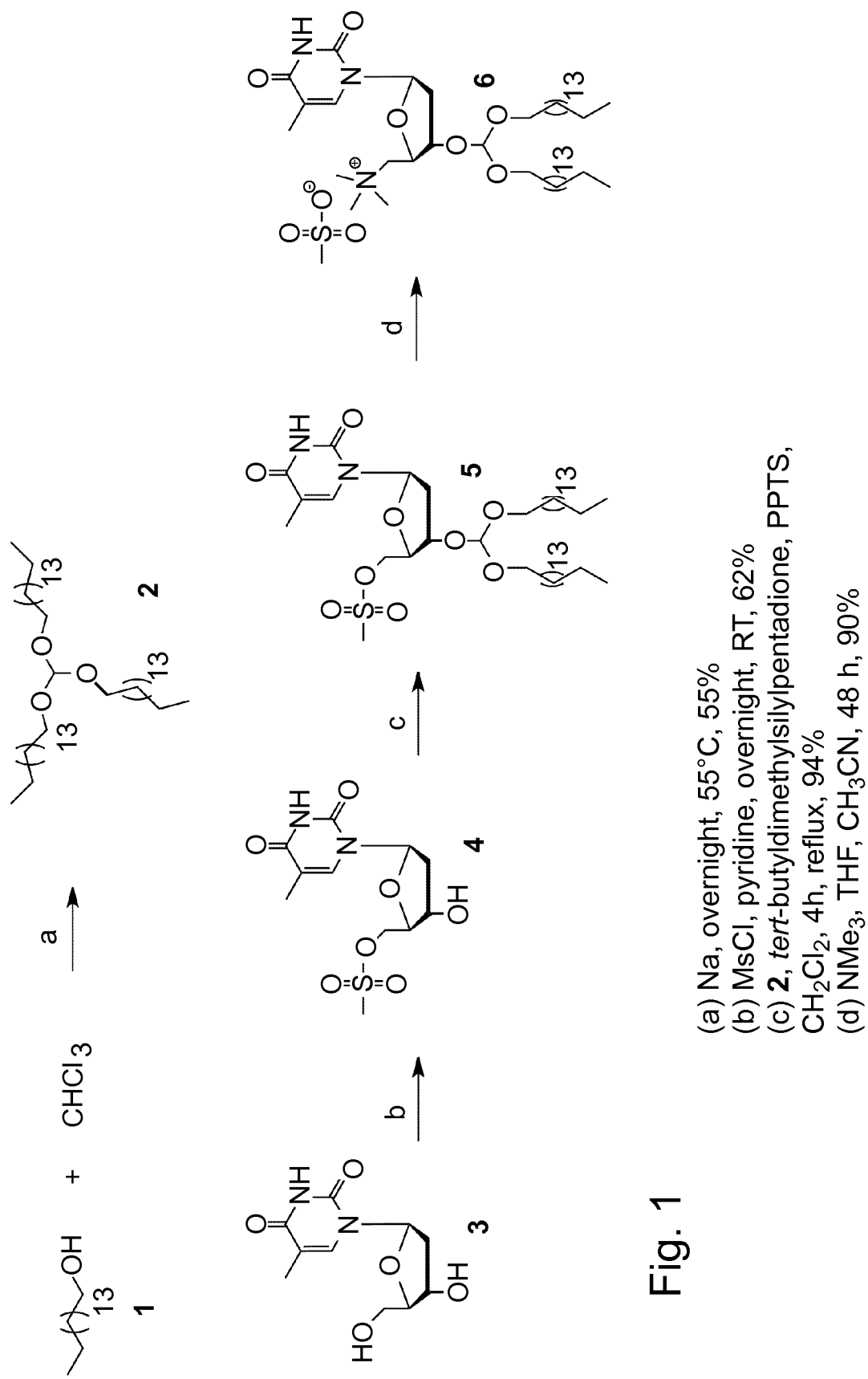
Figure 2:
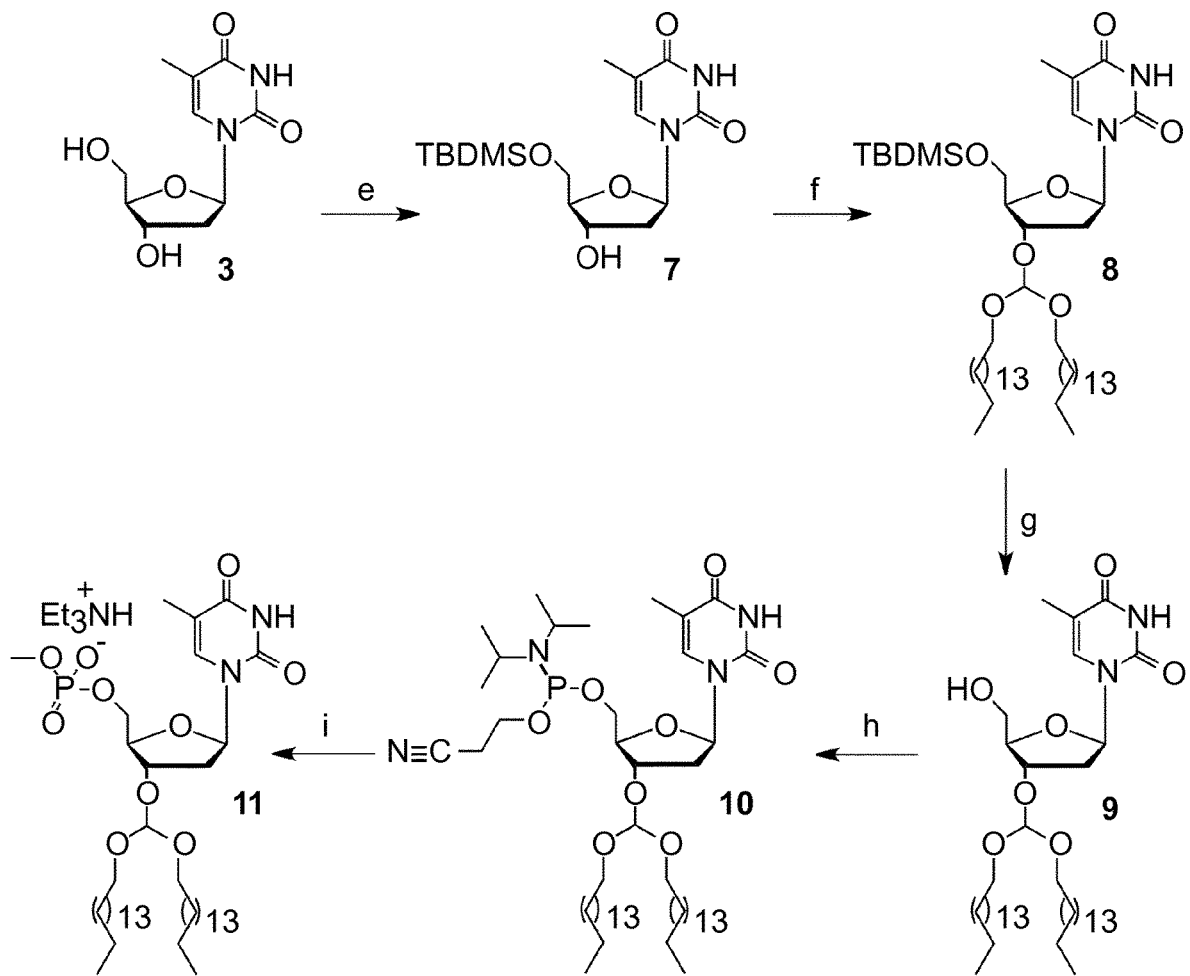
FIG. 2 shows the synthetic scheme used for Preparation 3 and examples 4, 5 and 6 (compounds of formula (I) bearing an anionic group at $R_3$).

1-hexadecanol (6.10 g, 25.16 mmol, 3 eq.) (compound 1 in FIG. 1) was heated at 55° C. then sodium (0.57 g, 25.16 mmol, 3 eq.) and chloroform (0.67 mL, 8.38 mmol, 1 eq.) were added. The mixture was stirred for overnight and diluted with hexane. After filtration, the solvent was removed under vacuum. The product 2 was isolated after purification using a LH20 size exclusion column in ($CH_2Cl_2/CH_3OH$: 50/50). Yield: 55%.

$^1$H NMR (300 MHz, $CDCl_3$): δ in ppm: 0.90 (t, J=6.9 Hz, 9H, $3CH_3$), 1.27 (m, 78H, $39CH_2$), 1.61 (m, 6H, $3CH_2$), 3.53 (m, 6H, $3CH_2$), 5.15 (s, 1H, CH).

$^{13}$C NMR (75 MHz, $CDCl_3$): δ in ppm: 14.14 ($CH_3$), 22.72 ($CH_2$), 26.23 ($CH_2$), 29.40-29.74 ($CH_2$), 31.95 ($CH_2$), 63.97 ($CH_2O$), 112.66 (CH).

PREPARATION 2

Compound 4

((2R,3S,5R)-3-hydroxy-5-(5-methyl-2,4-dioxo-3,4-dihydropyrimidin-1(2H)-yl)tetrahydrofuran-2-yl)methyl methanesulfonate

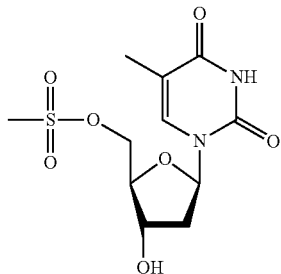

4

Thymidine (0.5 g, 2.06 mmol) was dissolved in 20 mL of dry pyridine and cooled to 0° C. Next, methanesulfonyl chloride (0.284 g, 2.07 mmol, 1.05 eq.) was added drop wise. The reaction mixture was stirred at room temperature for overnight. The next day, 5 mL of methanol was added to quench the reaction, then the solvent was evaporated under reduced pressure and the residual compound was purified by column chromatography (silica gel, $CH_2Cl_2/CH_3OH$: 90/10). Yield: 62%.

$^1$H NMR (300 MHz, DMSO-$d_6$): δ in ppm: 1.78 (s, 3H, $CH_3$), 2.15 (m, 2H, $H_{2'}$), 3.23 (s, 3H, $CH_3$), 3.98 (m, 1H, $H_{4'}$), 4.26 (m, 1H, $H_{3'}$), 4.38 (m, 2H, $H_{5'}$), 5.52 (d, J=4.1 Hz, 1H, OH), 6.23 (t, J=6.9 Hz, 1H, $H_{1'}$), 7.49 (s, 1H, CH), 11.36 (s, 1H, NH).

PREPARATION 3

Compound 7

1-((2R,4S,5R)-5-(((tert-butyldimethylsilyl)oxy)methyl)-4-hydroxytetrahydrofuran-2-yl)-5-methyl-pyrimidine-2,4(1H,3H)-dione

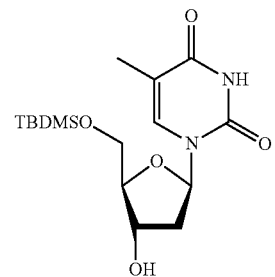

7

To a solution of thymidine 3 (see FIG. 1) (5 g, 20.6 mmol, 1.0 equiv.) in pyridine (125 mL) was added DMAP (0.126 g, 1.03 mmol, 0.05 equiv.) and TBDMSCl (3.48 g, 23.1 mmol, 1.1 equiv.) sequentially. The reaction mixture was stirred at room temperature for overnight. After removal of the solvent under reduced pressure, the crude reaction mixture was dissolved in DCM and successively washed by water and $NaHCO_3$ solution (5%) and brine. The organic layer then dried on $Na_2SO_4$ and evaporated under reduced pressure. The crude product was purified by column chromatography on silica gel. Compound 7 was isolated after purification on silica gel (ethyl acetate:hexane:TEA (80:20:1)) as white solid. Yield: 73%.

$^1$H NMR (300 MHz, $CDCl_3$): δ in ppm: 0.11 (s, 6H, $2CH_3$), 0.91 (s, 9H, $3CH_3$), 1.91 (s, 3H, $CH_3$), 2.08 (m, 1H, $H_{2'}$), 2.42 (m, 1H, $H_{2'}$), 3.69 (bs, 1H, OH), 3.87 (m, 2H, $H_{5'}$), 4.09 (m, 1H, $H_{3'}$), 4.44 (m, 1H, $H_{4'}$), 6.42 (t, J=6.8 Hz, 1H, $H_{1'}$), 7.56 (s, 1H, CH), 9.86 (s, 1H, NH).

$^{13}$C NMR (75 MHz, $CDCl_3$): δ in ppm: −5.45 ($CH_3$), −5.38 ($CH_3$), 12.56 ($CH_3$), 18.35 (CH), 25.92 ($3CH_3$), 41.13 ($C_{2'}$), 63.67 ($C_{5'}$), 72.54 ($C_{3'}$), 85.12 ($C_{4'}$), 87.50 ($C_{1'}$), 110.97 (C), 135.60 (CH), 150.78 (CO), 164.23 (CO).

Example 1

Compound 5

((2R,3S,5R)-3-(bis(hexadecyloxy)methoxy)-5-(5-methyl-2,4-dioxo-3,4-dihydropyrimidin-1(2H)-yl)tetrahydrofuran-2-yl)methyl methanesulfonate

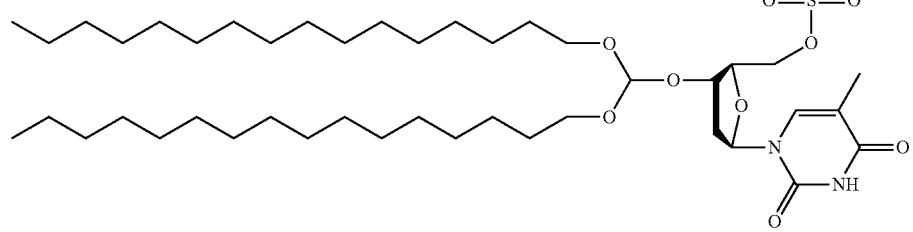

5

To a solution of compound 4 obtained in preparation 2 (0.15 g, 0.46 mmol), Compound 2 obtained in Preparation 1 (1.03 g, 1.39 mmol, 3 eq.) and tert-butyldimethylsilylpentadione (276 μL, 1.15 mmol, 2.5 eq.) in a mixture of $CH_2Cl_2$/DMF: 2/1 (6 mL) was added pyridinium p-toluenesulfonate (0.03 g, 0.13 mmol, 0.25 eq.). The mixture was stirred at reflux for 4 h. The reaction was neutralized with N,N,N',N'-tetramethylethylenediamine (35 μL, 0.23 mmol, 0.5 eq.) and methylene chloride was removed under vacuum. The residual compound was purified by column chromatography (silica gel, $CH_2Cl_2$/$CH_3OH$/TEA from 99/0/1 to 98/1/1). Yield: 94%.

$^1$H NMR (300 MHz, $CDCl_3$): δ in ppm: 0.89 (t, J=6.9 Hz, 6H, 2$CH_3$), 1.26 (m, 52H, 26$CH_2$), 1.60 (m, 4H, 2$CH_2$), 1.96 (s, 3H, $CH_3$), 2.18 (m, 1H, $H_{2'}$), 2.45 (m, 1H, $H_{2'}$), 3.08 (s, 3H, $CH_3$), 3.54 (m, 4H, 2$CH_2$), 4.26 (m, 1H, $H_{4'}$), 4.42 (dd, J=11.1 Hz, J=3.4 Hz, 1H, $H_{5'}$), 4.54 (dd, J=11.2 Hz, J=2.7 Hz, 1H, $H_{5'}$), 4.60 (m, 1H, $H_{3'}$), 5.10 (s, 1H, CH), 6.32 (t, J=6.6 Hz, 1H, $H_{1'}$), 7.37 (d, J=1.4 Hz, 1H, CH), 8.87 (s, 1H, NH).

$^{13}$C NMR (75 MHz, $CDCl_3$): δ in ppm: 12.43 ($CH_3$), 14.15 ($CH_3$), 22.71 ($CH_2$), 26.12 ($CH_2$), 29.38-29.72 ($CH_2$), 31.94 ($CH_2$), 37.69 ($CH_3$), 38.38 ($C_{2'}$), 65.46 ($CH_2O$), 65.62 ($CH_2O$), 68.76 ($C_{5'}$), 71.23 ($C_{3'}$), 82.45 ($C_{4'}$), 84.93 ($C_{1'}$), 111.66 (C), 112.70 (CH), 138.97 (CH), 150.24 (CO), 163.85 (CO).

Example 2

Compound 6

1-((2R,3S,5R)-3-(bis(hexadecyloxy)methoxy)-5-(5-methyl-2,4-dioxo-3,4-dihydropyrimidin-1 (2H)-yl) tetrahydrofuran-2-yl)-N,N,N-trimethyl-methanaminium methanesulfonate

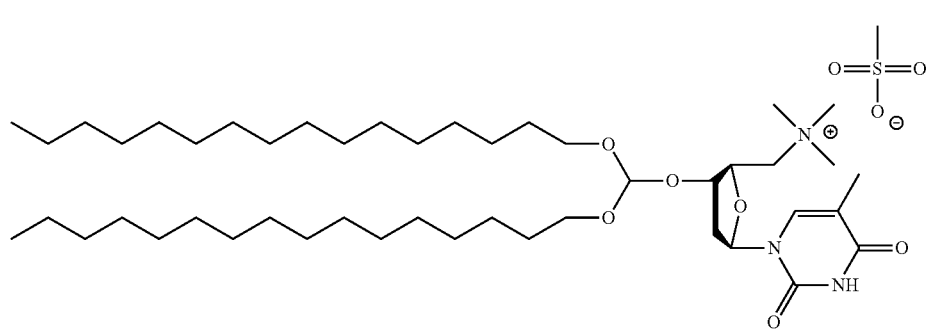

6

Anhydrous trimethylamine (2 mL) was transferred to a pressure tube cooled at −50° C. via a syringe. Next, anhydrous acetonitrile (2 mL) and a solution of compound 5 obtained in example 1 (0.16 g, 0.2 mmol) in dry THF (2 mL) were added. The tube was sealed and heated in an oil bath at 50° C. during 48 h and then cooled to −20° C. and opened. The solvents were evaporated under reduced pressure to give compound 6 as a white solid. Yield: 90%.

$^1$H NMR (300 MHz, $CDCl_3$): δ in ppm: 0.89 (t, J=6.9 Hz, 6H, 2$CH_3$), 1.26 (m, 52H, 26$CH_2$), 1.58 (m, 4H, 2$CH_2$), 2.00 (s, 3H, $CH_3$), 2.30 (m, 1H, $H_{2'}$), 2.62 (m, 1H, $H_{2'}$), 2.79 (s, 3H, $CH_3$), 3.35 (s, 9H, 3$CH_3$), 3.53 (m, 4H, 2$CH_2$), 3.66 (m, 1H, $H_{5'}$), 4.40-4.69 (m, 3H, $H_{3'}$, $H_{4'}$, $H_{5'}$), 5.22 (s, 1H, CH), 6.29 (t, J=6.6 Hz, 1H, $H_{1'}$), 7.73 (s, 1H, CH), 9.12 (s, 1H, NH).

$^{13}$C NMR (75 MHz, $CDCl_3$): δ in ppm: 11.65 ($CH_3$), 13.66 ($CH_3$), 22.23 ($CH_2$), 25.63 ($CH_2$), 28.90-29.25 ($CH_2$), 31.45 ($CH_2$), 35.80 ($C_{2'}$), 39.28 ($CH_3$), 53.75 ($CH_3$), 64.84 ($CH_2O$), 65.22 ($CH_2O$), 66.86 ($C_{5'}$), 74.24 ($C_{3'}$), 78.79 ($C_{4'}$), 87.08 ($C_{1'}$), 111.43 (C), 112.56 (CH), 137.32 (CH), 150.49 (CO), 163.74 (CO).

Example 3

Compound 8

1-((2R,4S,5R)-4-(bis(hexadecyloxy)methoxy)-5-((((tert-butyldimethylsilyl)oxy)methyl)tetrahydrofuran-2-yl)-5-methylpyrimidine-2,4(1H,3H)-dione

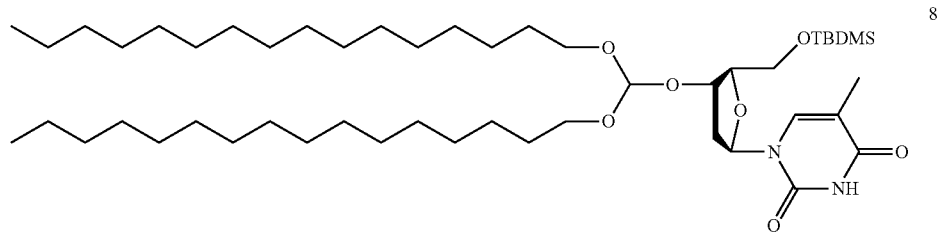

8

To a solution of compound 7 obtained in preparation 3 (0.3 g, 0.84 mmol), Compound 2 obtained in preparation 1 (1.86 g, 2.52 mmol, 3 eq.) and tert-butyldimethylsilylpentadione (497 µL, 2.1 mmol, 2.5 eq.) in 10 mL of anhydrous methylene chloride was added pyridinium p-toluenesulfonate (0.052 g, 0.21 mmol, 0.25 eq.). The mixture was stirred at reflux for 4 h. The reaction was neutralized with N,N,N',N'-tetramethylethylenediamine (63 µL, 0.42 mmol, 0.5 eq.) and methylene chloride was removed under vacuum. The residual compound was purified by column chromatography (silica gel, $CH_2Cl_2/CH_3OH/TEA$ from 99/0/1 to 98.5/0.5/1). Yield: 83%.

$^1$H NMR (300 MHz, $CDCl_3$): δ in ppm: 0.13 (s, 6H, $2CH_3$), 0.89 (t, J=6.3 Hz, 6H, $2CH_3$), 0.94 (s, 9H, $3CH_3$), 1.26 (m, 52H, $26CH_2$), 1.59 (m, 4H, $2CH_2$), 1.93 (s, 3H, $CH_3$), 2.02 (m, 1H, $H_{2'}$), 2.42 (m, 1H, $H_{2'}$), 3.52 (m, 4H, $2CH_2$), 3.85 (m, 2H, $H_{5'}$), 4.16 (m, 1H, $H_{3'}$), 4.52 (m, 1H, $H_{4'}$), 5.19 (s, 1H, CH), 6.35 (t, J=6.9 Hz, 1H, $H_{1'}$), 7.52 (s, 1H, CH), 8.92 (s, 1H, NH).

$^{13}$C NMR (75 MHz, $CDCl_3$): δ in ppm: −5.46 ($CH_3$), −5.34 ($CH_3$), 12.55 ($CH_3$), 14.15 ($CH_3$), 18.38 (CH), 22.71 ($CH_2$), 25.94 ($CH_3$), 26.21 ($CH_2$), 29.38-29.72 ($CH_2$), 31.95 ($CH_2$), 39.08 ($C_{2'}$), 63.29 ($C_{5'}$), 64.76 ($CH_2O$), 64.96 ($CH_2O$), 73.03 ($C_{3'}$), 84.90 ($C_{4'}$), 85.75 ($C_{1'}$), 110.83 (C), 112.66 (CH), 135.41 (CH), 150.27 (CO), 164.84 (CO).

Example 4

Compound 9

1-((2R,4S,5R)-4-(bis(hexadecyloxy)methoxy)-5-(hydroxymethyl)-tetrahydrofuran-2-yl)-5-methylpyrimidine-2,4(1H,3H)-dione

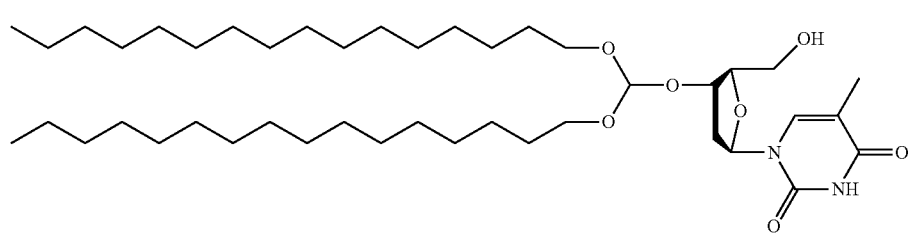

9

To a solution of compound 8 (0.3 g, 0.35 mmol) in 4 mL of dry THF was added tetra-n-butylammonium fluoride (680 μL, 0.7 mmol, 2 eq.). The reaction mixture was stirred for 1 h at room temperature and the solvent was removed under vacuum. The residual compound was purified by column chromatography (silica gel, $CH_2Cl_2/CH_3OH/TEA$: 98/1/1). Yield: 94%.

$^1$H NMR (300 MHz, $CDCl_3$): δ in ppm: 0.89 (t, J=6.9 Hz, 6H, $2CH_3$), 1.27 (m, 52H, $26CH_2$), 1.60 (m, 4H, $2CH_2$), 1.93 (s, 3H, $CH_3$), 2.39 (m, 2H, $H_{2'}$), 3.54 (m, 4H, $2CH_2$), 3.82 (dd, J=11.9 Hz, J=2.9 Hz, 1H, $H_{5'}$), 3.94 (dd, J=11.9 Hz, J=2.6 Hz, 1H, $H_{5'}$), 4.12 (m, 1H, $H_{3'}$), 4.61 (m, 1H, $H_{4'}$), 5.21 (s, 1H, CH), 6.16 (t, J=6.6 Hz, 1H, $H_{1'}$), 7.39 (s, 1H, CH).

$^{13}$C NMR (75 MHz, $CDCl_3$): δ in ppm: 12.53 ($CH_3$), 14.13 ($CH_3$), 22.69 ($CH_2$), 26.14 ($CH_2$), 29.33-29.71 ($CH_2$), 31.92 ($CH_2$), 38.31 ($C_{2'}$), 62.10 ($C_{5'}$), 64.97 ($CH_2O$), 65.12 ($CH_2O$), 72.19 ($C_{3'}$), 85.37 ($C_{4'}$), 86.45 ($C_{1'}$), 111.00 (C), 112.64 (CH), 136.87 (CH), 150.45 (CO), 164.04 (CO).

Example 5

Compound 10

((2R,3S,5R)-3-(bis(hexadecyloxy)methoxy)-5-(5-methyl-2,4-dioxo-3,4-dihydropyrimidin-1 (2H)-yl) tetrahydrofuran-2-yl)methyl (2-cyanoethyl) diisopropylphosphoramidite

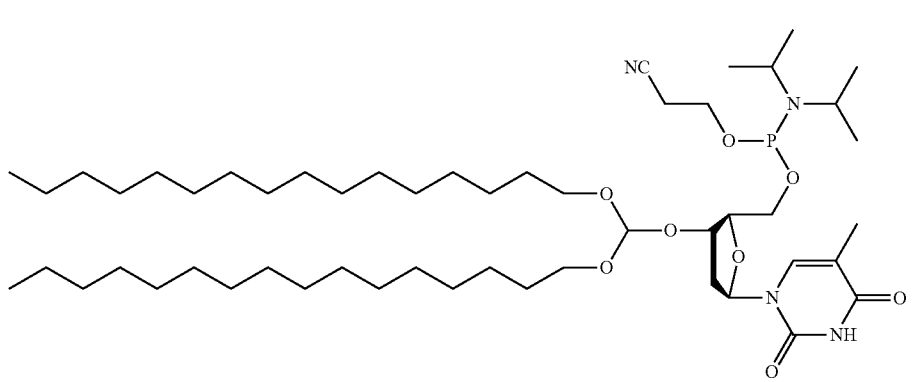

Compound 9 obtained in example 4 was dried over $P_2O_5$ overnight under reduced pressure before use. Compound 9 (0.45 g, 0.61 mmol), Diisopropylethylamine (212 μL, 1.22 mmol, 2 eq.) and 2-Cyanoethyl N,N-diisopropylchlorophosphoramidite (204 μL, 0.91 mmol, 1.5 eq.) were dissolved in 10 mL of dry dichloromethane and the solution stirred at room temperature for 1 h. Sodium bicarbonate 0.1M (5 mL) was poured into the flask and the aqueous phase extracted with dichloromethane. The residual compound was purified by column chromatography (silica gel, $CH_2Cl_2/CH_3OH/$ TEA from 99/0/1 to 98/1/1). Yield: 93%.

$^1$H NMR (300 MHz, $CDCl_3$): δ in ppm: 0.88 (t, J=6.6 Hz, 6H, $2CH_3$), 1.19 (m, 12H, iPr), 1.25 (m, 54H, $27CH_2$), 1.58 (m, 6H, $3CH_2$), 1.93 (s, 3H, $CH_3$), 2.05 (m, 1H, $H_{2'}$), 2.44 (m, 1H, $H_{2'}$), 2.65 (m, 2H, iPr), 3.61 (m, 2H, $CH_2CN$), 3.85 (m, 4H, $OCH_2$, $H_5$), 4.24 (m, 1H, $H_{3'}$), 4.53 (m, 1H, $H_{4'}$), 5.19 (s, 1H, CH), 6.32 (m, 1H, $H_{1'}$), 7.51 (s, 0.5H, CH, dia1), 7.65 (s, 0.5H, CH, dia2).

$^{31}$P NMR (121 MHz, $CDCl_3$): δ in ppm: 152.05

Example 6

Compound 11

((2R,3S,5R)-3-(bis(hexadecyloxy)methoxy)-5-(5-methyl-2,4-dioxo-3,4-dihydropyrimidin-1(2H)-yl)tetrahydrofuran-2-yl)methyl methyl phosphate

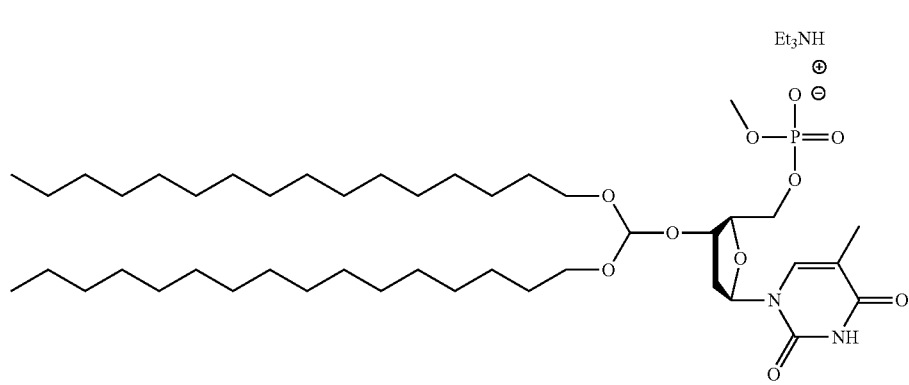

Phosphoramidite 10 obtained in example 10 (0.2 mg, 0.21 mmol), methanol (13 µL, 0.31 mmol, 1.5 eq.) were dissolved in 3 mL of dry THF and a tetrazole solution in acetonitrile (0.45 M, 0.7 mL, 0.27 mmol, 1.3 eq.) was added under argon. The reaction mixture was stirred for 1 h at room temperature followed by oxidation with 20 mL of a solution of $I_2$ (0.02 M in THF/Pyr/$H_2O$)(pH=7.4). After 5 h at room temperature, the solvent was evaporated under high vacuum to yield intermediate products. The contents of the reaction flask were dissolved in 20 mL of ethyl acetate and then washed with 3×10 mL of a saturated solution of $Na_2S_2O_3$. After removal of the solvent under reduced pressure, the crude reaction mixture was dissolved in a mixture of $CH_2Cl_2$/TEA: 9/1 (10 mL), stirred at room temperature for overnight and the solvent was removed under vacuum. The residual compound was purified by column chromatography (silica gel, $CH_2Cl_2$/$CH_3OH$/TEA from 98/1/1 to 94/5/1). Yield: 65%.

$^1$H NMR (300 MHz, CDCl$_3$): δ in ppm: 0.86 (t, J=6.6 Hz, 6H, 2CH$_3$), 1.23 (m, 56H, 28CH$_2$), 1.55 (m, 4H, 2CH$_2$), 1.95 (s, 3H, CH$_3$), 2.18 (m, 1H, H$_{2'}$), 2.35 (m, 1H, H$_{2'}$), 2.91 (q, J=7.2 Hz, J=14.5 Hz, 6H, 3CH$_2$), 3.50 (m, 4H, 2CH$_2$), 3.59 (d, J=10.7 Hz, 3H, P—OCH$_3$), 4.05 (m, 2H, H$_{5'}$), 4.19 (m, 1H, H$_{3'}$), 4.57 (m, 1H, H$_{4'}$), 5.17 (s, 1H, CH), 6.38 (t, J=6.5 Hz, 1H, H$_{1'}$), 7.81 (s, 1H, CH).

$^{13}$C NMR (75 MHz, CDCl$_3$): δ in ppm: 9.24 (CH$_3$), 12.34 (CH$_3$), 14.07 (CH$_3$), 22.64 (CH$_2$), 26.11 (CH$_2$), 29.32-29.66 (CH$_2$), 31.90 (CH$_2$), 38.61 (C$_{2'}$), 45.62 (CH$_2$), 52.59 et 52.69 (d, J=5.6 Hz, P—OCH$_3$), 64.68 et 64.73 (d, J=3.5 Hz, C$_{5'}$), 67.90 (CH$_2$O), 73.92 (C$_{3'}$), 84.44 et 84.56 (d, J=8.4 Hz, C$_{4'}$), 84.69 (C$_{1'}$), 111.07 (C), 112.65 (CH), 136.36 (CH), 150.54 (CO), 164.02 (CO).

$^{31}$P NMR (121 MHz, CDCl$_3$): δ in ppm: 4.08

Example 7

Compound 12

((2R,3S,5R)-3-(bis(hexadecyloxy)methoxy)-5-(5-methyl-2,4-dioxo-3,4-dihydropyrimidin-1 (2H)-yl)tetrahydrofuran-2-yl)methyl O-Methyl-O'-succinyl-polyethyleneglycol 500

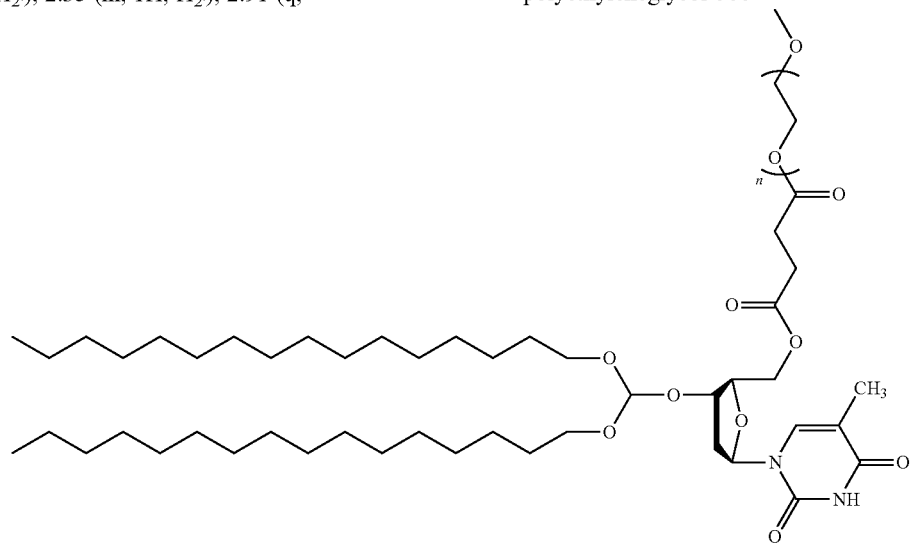

O-Methyl-O'-succinylpolyethyleneglycol 500 (105 mg, 0.176 mmol), compound 9 prepared in example 4 (130 mg 0.176 mmol), N,N'-Dicyclohexylcarbodiimide (73 mg, 0.352 mmol), and 4-(Dimethylamino)pyridine (43 mg, 0.352 mmol), were dried for 1 h under high vacuum. The compounds were then dissolved under nitrogen in 4 mL of anhydrous methylene chloride. The mixture was stirred for overnight at room temperature under nitrogen. The DCU was filtered and the solvent was removed. The product was isolated after purification using a LH20 size exclusion column in (DCM/MeOH 50:50). Yield: 72%.

$^1$H NMR (300 MHz, CDCl$_3$): δ in ppm: 0.89 (t, J=6.9 Hz, 6H, 2CH$_3$), 1.26 (m, 52H, 26CH$_2$), 1.58 (m, 4H, 2CH$_2$), 1.94 (s, 3H, CH$_3$), 2.12 (m, 1H, H$_{2'}$), 2.47 (m, 1H, H$_{2'}$), 2.68 (m, 4H, 2CH$_2$), 3.39 (s, 3H, CH$_3$), 3.54 (m, 6H, 3CH$_2$), 3.65 (m, H$_{3'}$, CH$_2$—PEG), 4.25 (m, 3H, H$_{5'}$, CH$_2$), 4.35 (m, 1H, H$_{5'}$), 4.45 (m, 1H, H$_{4'}$), 5.18 (s, 1H, CH), 6.27 (t, J=6.6 Hz, 1H, H$_{1'}$), 7.40 (s, 1H, CH), 8.48 (s, 1H, NH).

Example 8

Preparation of Anionic and Cationic Liposomes and Liposome Characterization

100 µL of stock solutions of anionic or cationic compounds of formula (I) prepared in examples 2 and 6 (10 mg/mL in dichloromethane) were placed in glass tubes, dried under dry N$_2$ and then desiccated under vacuum. Milli-Q Water was added to the dried lipid to obtain liposomes dispersions (1 mg/mL) after vortex agitation and sonication for 10 min.

Figure 3A:
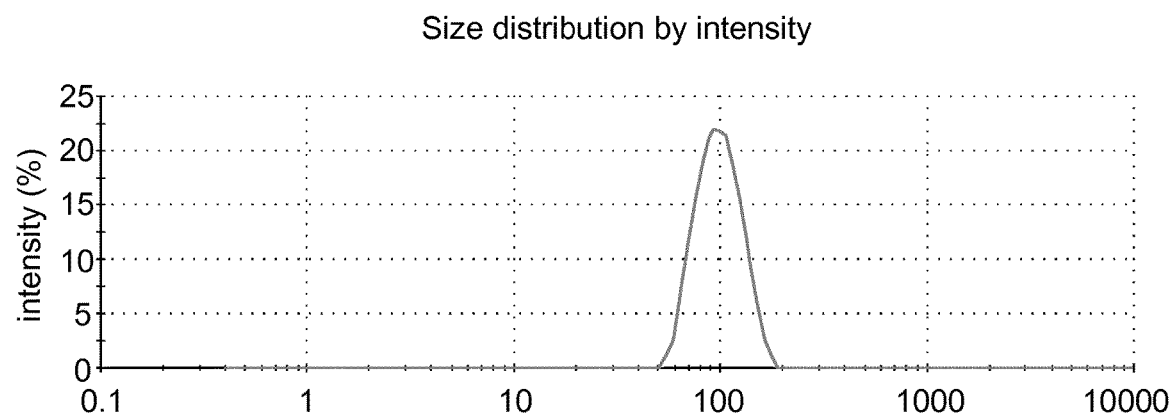
FIGS. 3A and 3B show the size distribution measured by dynamic light scattering (DLS) of liposomes prepared respectively from anionic compounds of formula (I) and of liposomes prepared from cationic compounds of formula (I).
Figure 3B:
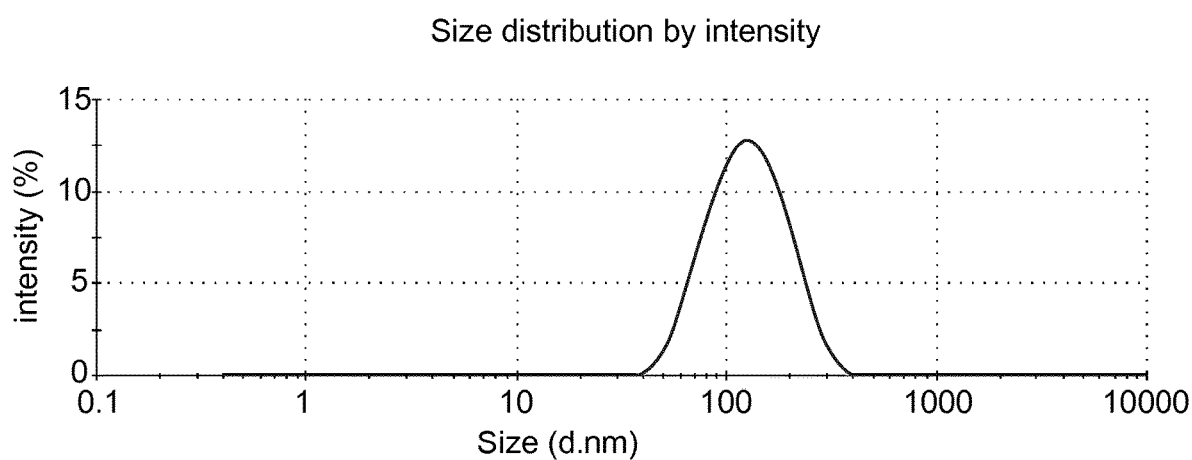

The size distribution by intensity measured by dynamic light scattering (DLS) of liposomes prepared from compound 11 prepared in example 6 (anionic compounds of formula (I)) is shown on FIG. 3A, and of liposomes prepared from compound 6 prepared in example 2 (cationic compound of formula (I)) is shown on FIG. 3B.

The results show that the compounds of formula (I) form supramolecular assemblies of similar size in aqueous solution with reasonably narrow polydispersity.

Figure 4A:
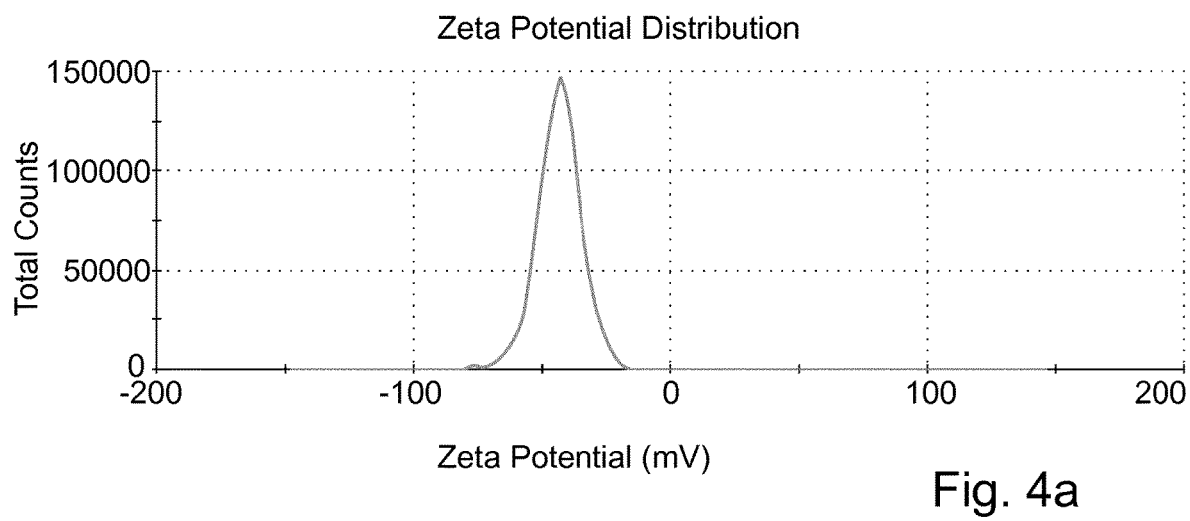
FIGS. 4A and 4B show the zeta potential of liposomes prepared respectively from anionic and cationic compounds of formula (I).

The zeta potential of liposomes prepared from anionic compound 11 prepared in example 6 is shown on FIG. 4A.
d=100.4 nm
Pdi=0.163
ζ=−43.3 mV
where d is the diameter in nanometer, Pdi is the polydispersity and ζ is the zeta potential in mV.

Figure 4B:
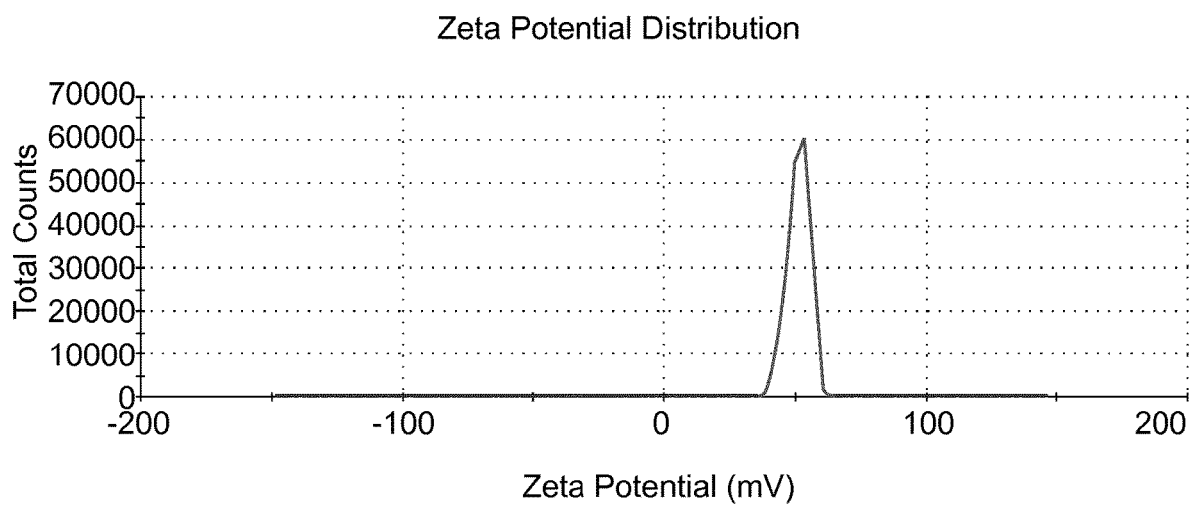

The zeta potential of liposomes prepared from cationic compound 6 prepared in example 2 is shown on FIG. 4B.
d=135.9 nm
Pdi=0.221
ζ=51.4 mV
where d is the diameter in nanometer, Pdi is the polydispersity and ζ is the zeta potential in mV.

The results show that the zeta potential measured for liposomes based on anionic or cationic compounds of formula (I) depends on the charge of the respective polar head. Thus, the presence of orthoester function has a limited effect on the formation of aggregates.

Example 9

NMR Kinetic Studies and Hydrolysis Profiles

1HNMR experiments were performed to study the kinetics of hydrolysis for both anionic and cationic compounds of formula (I) at pH 5 and 7.4 by measuring the percentage of hydrolyzed compound versus time.

10 mg of cationic compound (6) prepared in example 2 or anionic compound (11) prepared in example 6 were dissolved in a mixture of MeOD:Buffer phosphate (1:2) (pH 5 or 7.4), mixed and placed in a NMR tube. $^1$H NMR Experiment was performed at 37° C. at 300 MHz on a BRUKER® Avance DPX-300.

Figure 5:
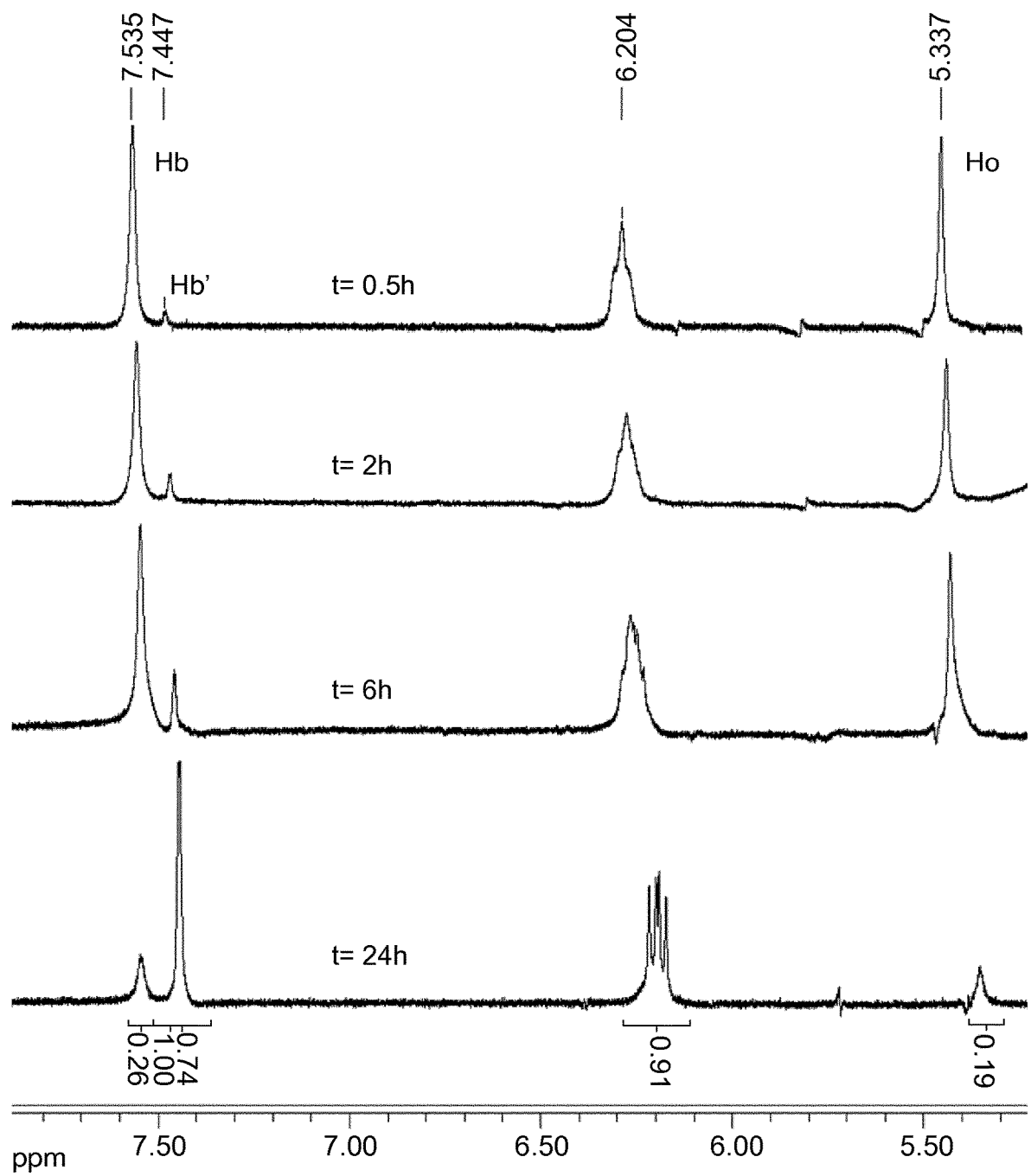
FIG. 5 shows the $^1$H NMR study of cationic compound (6) after incubation at pH=5 at 37° C. for different time periods

The $^1$H NMR study of cationic compound (6) after incubation at pH=5 at 37° C. for different time periods is shown on FIG. 5.

Figure 6:
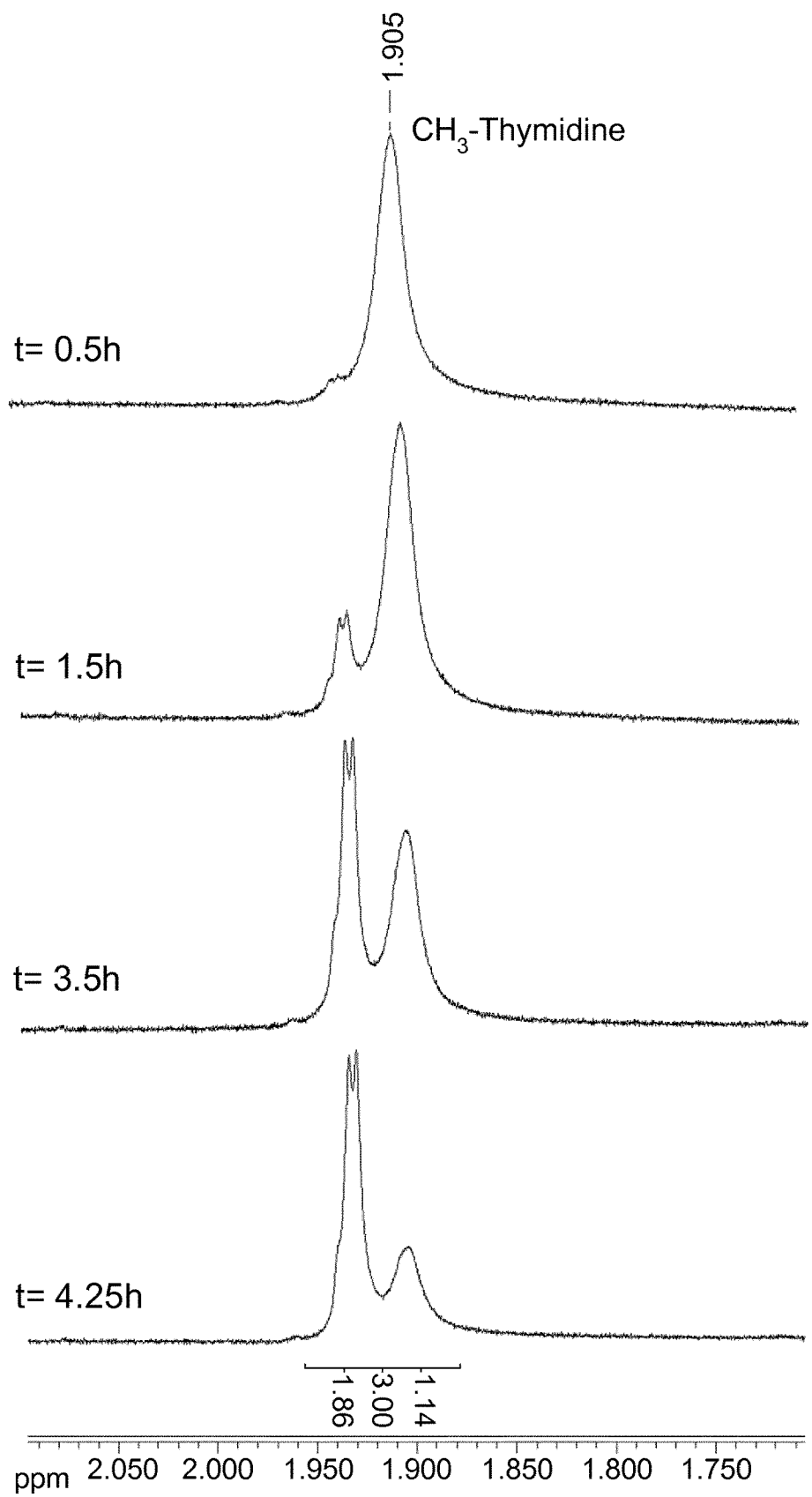
FIG. 6 shows the $^1$H NMR study of anionic compound (11) after incubation at pH=7.4 at 37° C. for different time periods.

The $^1$H NMR study of anionic compound (11) after incubation at pH=7.4 at 37° C. for different time periods is shown on FIG. 6.

After hydrolysis of the orthoester function, the chemical shifts of the thymidine CH$_3$ protons are shifted upfield and downfield for compound 6 and 11, respectively. Thus, the percentage of hydrolysis versus time was followed by integrating the signals of the CH$_3$ protons.

Figure 7:
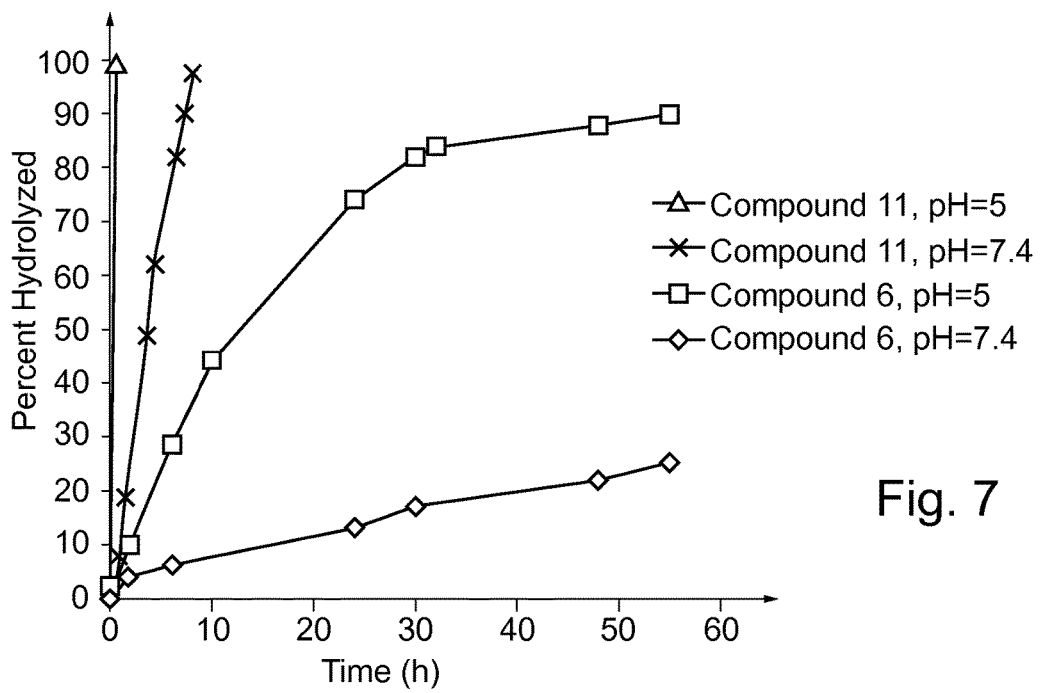
FIG. 7 shows the hydrolysis profile of cationic compound (6) and anionic compound (11) as a function of time at different pH at 37° C.

The hydrolysis profile of cationic compound 6 and anionic compound 11 as a function of time at different pH at 37° C. is shown on FIG. 7.

The results show that the hydrolysis rate of the orthoester function depends on both the pH and charge of the polar heads. The rate of hydrolysis of the orthoester function is known to increase with the hydrogen ion concentration. Hence, both compounds 6 and 11 show higher rates of hydrolysis at pH=5. The increased hydrolysis rates observed for the anionic compound 11 relative to cationic compound 6 at both pH 5 and 7 results from the presence of a negative charge in the orthoester headgroup.

Example 10

Preparation of Liposomes Formed from Cationic Compounds of Formula (I) and Dioleylphosphatidylcholine (DOPC) and Study of Colloidal Stability Stock solutions of compound 11 prepared in example 6 (anionic compounds of formula (I)) or compound 6 prepared in example 2 (cationic compounds of formula (I)) (10 mg/mL in dichloromethane) and DOPC (10 mg/mL in dichloromethane) (1:1) were mixed and placed in glass tubes. The mixture was dried under dry N$_2$ and then desiccated under vacuum. Buffer (pH 5) was added to the dried lipids to obtain liposomes dispersions (5 mg/mL) after vortex agitation. Then the mixture was heated to 37° C. for 48 h.

The colloidal stability of the liposomes (orthoester/DOPC, 1/1) are studied by dynamic light scattering (Diameter and PDI of particles versus time).

Figure 8A:
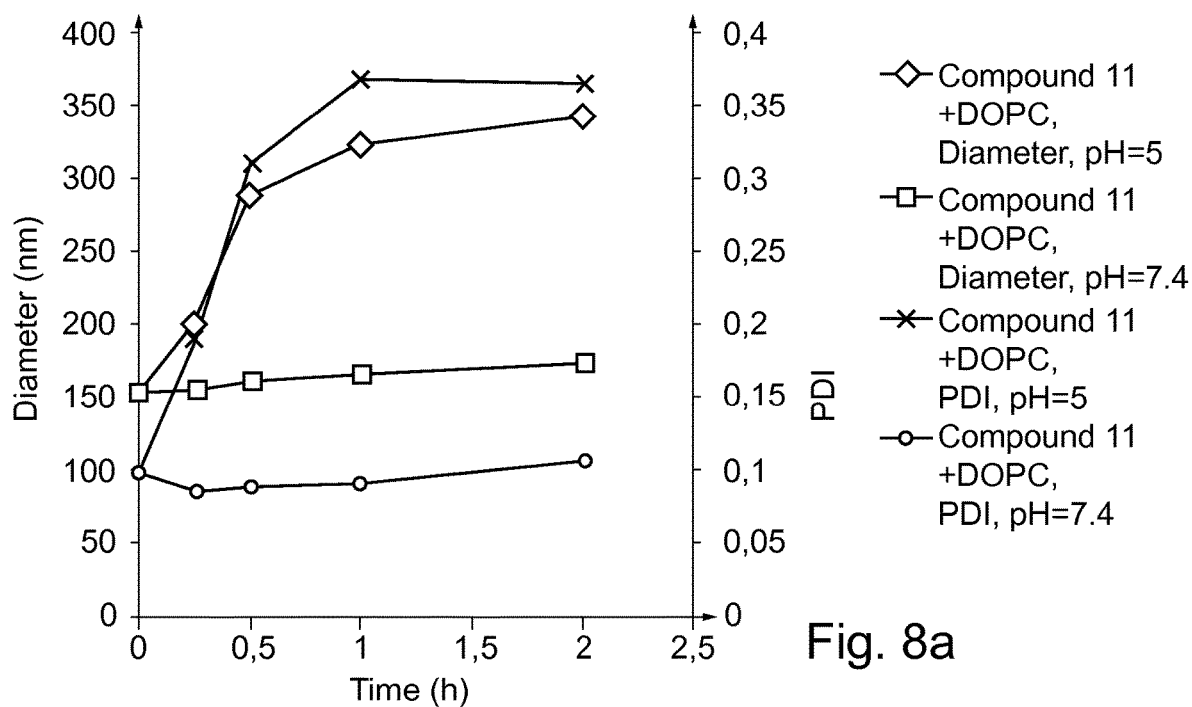
FIGS. 8A and 8B show the colloidal stability of liposomes formed respectively from anionic compounds of formula (I)/DOPC and cationic compounds of formula (I)/DOPC).
Figure 8B:
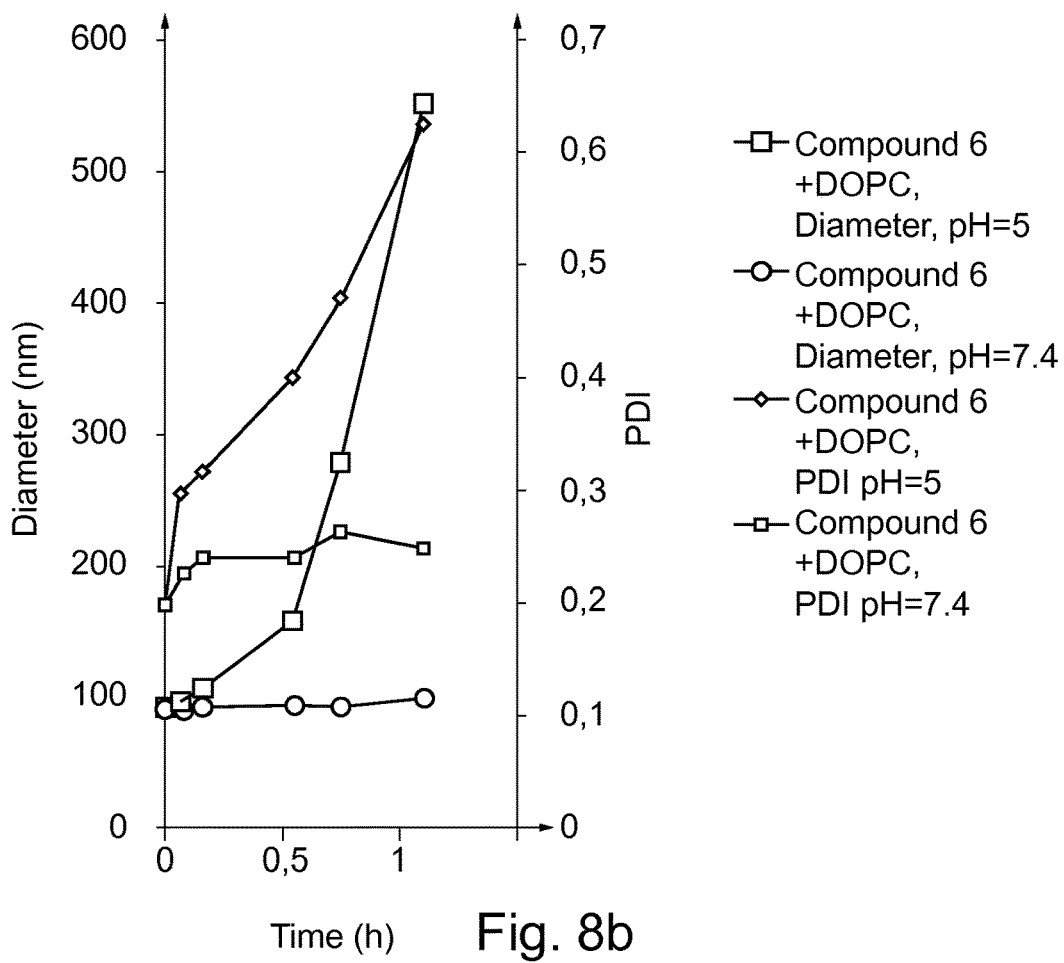

The results are shown on FIG. 8A (anionic compounds/DOPC) and FIG. 8B (cationic compounds/DOPC).

The results show that hydrolysis of the orthoester function results in an increase of the particles' diameter. The polydispersity index increases when the diameter increases. At pH 7.4 (37° C.) the colloidal stability is maintained for more than 2 hours, whereas in acidic conditions (pH 5, 37° C.) both the sizes and polydispersity indexes increase versus time, indicating a disruption of the colloidal suspension.

Example 11

Small-Angle X-Ray Scattering (SAXS) Experiments

Samples containing mixture of compound 6/DOPC (1/1, w/w), after preparation, were carefully transferred at room temperature into sealed quartz capillaries. SAXS experiments were carried out at the Centre de Recherche Paul Pascal, Pessac, France on a NanoStar (Bruker). With a sample to detector distance equal to 650 mm and a radiation wavelength of A=0.154 nm, the scattering wave vectors in reciprocal space ranged from q=0.16 nm$^{-1}$ and 3.4 nm$^{-1}$.

The total resolution of detection was estimated by fitting Gaussian functions to peaks from silver behenate diffractograms; the value of Aq was found to be ca. 3.1×10−2 nm$^{-1}$. The beam size at the sample position was 0.45 mm (0). Images were captured by the HiStar (Bruker).

The array of detection totalizes 1024×1024 pixels, each one with 100 μm for side. Data were radially averaged and corrected for background scattering by using the software SAXS-Bruker. All experiments were carried out on thermally equilibrated samples at 25° C., which was obtained by keeping the sample holders under water circulation at controlled temperature.

The results reported on FIG. 10 show that that the SAXS profile of compound 6 (cationic compound)/DOPC (mol ratio 50/50) before (•) and after (□) incubation at pH=5 and 37° C. evolves from vesicular to multilamellar systems.

Example 12

Inhibition of RECQL4 by siRNA

RECQL4 is a human RecQ helicase implicated in three syndromes (Rothmund-Thompson, RAPADILINO and Baller-Gerold) displaying accelerating aging, developmental abnormalities and cancer's predisposition. An increased of RECQL4 mRNA level was observed in clinical breast tumor samples and recent studies indicate that overexpression of RECQL4 play a critical role in human breast tumor luminal B progression. In this example, the efficacy of compound 6 prepared in example 2 in the transfection of siRNA targeting RECQL4 is evaluated.

Compound 6 and DOPE were mixed with molar ratio and dissolved in methylene chloride. The solvent was evaporated with nitrogen flow while stirring to prepare lipids films. This preparation was rehydrated with 1 mL of water, them submitted to Vortex, and the tube was put in ultrasonic bath (37 kHz) during 15-20 min at 15° C. The same experiment was carried out with DOTAU/DOPE (1:1)

Liposomes were analysed by DLS (Malvern, Zetasizer) and measured 74 nm of diameters for orthoester and 48 nm for DOTAU.

10 pmol of siRNA were added to 2 nmol of orthoester/DOPE in 100 μL of PRMI 1640 serum-free medium. After submitting to Vortex, this solution was incubated 20 min at RT and transferred in wells. The siRNA orthoester/DOPE complexes were analysed by DLS and measured at 90 nm with siRNA luciferase and at 100 nm with siRNA RECQL4 for orthoester (69 nm and 63 nm, respectively for DOTAU).

2.10$^5$ MDA-MB-134 cells by well were added in 500 μL final volume. Cells were cultivated during 72 h after transfection.

Confluent cells were washed with PBS buffer and lysed by 0.5 mL of Trizol (Invitrogen). 200 μL of chloroform/isoamylalcool (25:1) were added. After centrifugation during 10 min at 14000 rpm, 4° C. the aqueous phase containing RNA was collected.

RNA was precipitated overnight at −20° C. with 250 μL of isopropanol and 3 μL of Glycoblue (Ambion). After centrifugation during 30 min at 14000 rpm, 4° C., the pellet was washed with ethanol 75% and finally dissolved in 10 μL of water.

RNA was converted in cDNA by Reverse Transcription with QuantiTect kit (Qiagen). Then, a quantitative PCR was performed with 25 ng of cDNA, the master mix GoTaq qPCR (Promega) and specific primers (1 μM). Ct were normalized by the expression of GAPDH.

Each condition was done in triplicate.

Figure 9:
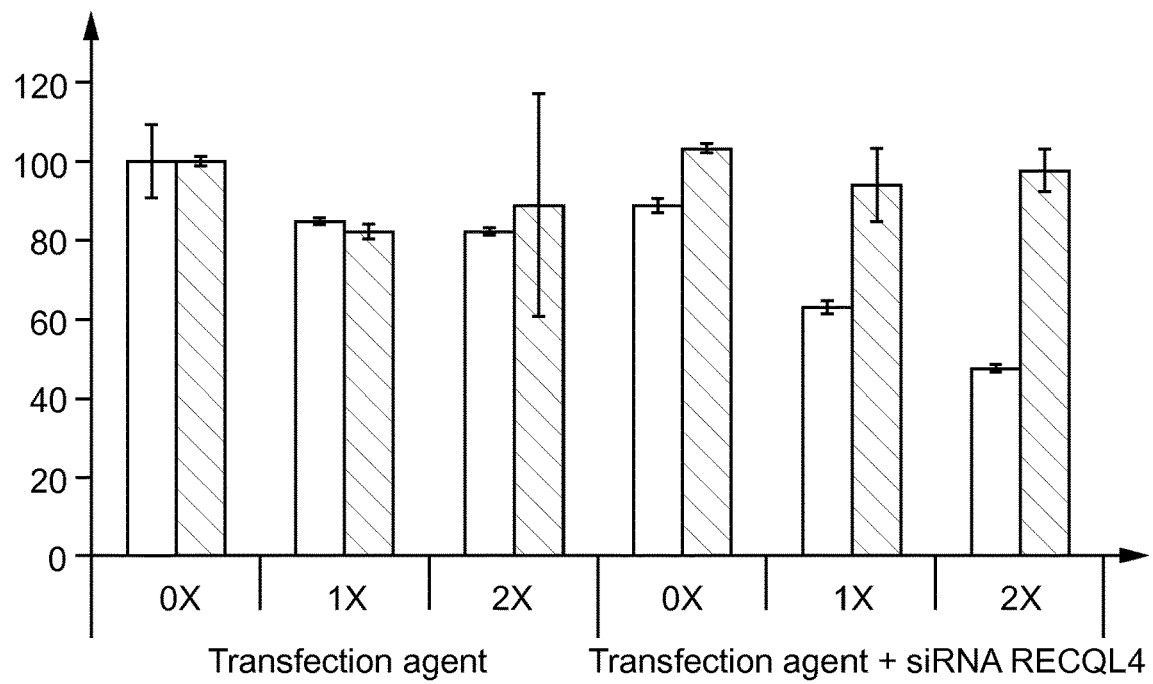
FIG. 9 shows the inhibition of RECQL4 by siRNA using complexes involving cationic compounds of formula (I) for transfection.

The results are reported on FIG. 9, showing the expression levels of RECQL4 normalized with GAPDH (Breast Cancer cells MDA-MB-134).

X correspond to concentration of nucleolipids (Orthoester (white column) or DOTAU (striped column)); 1X: N/P=1/5, 2X: N/P=1/10. The ratios N/P correspond to the ratios of ammonium (cationic lipids)/phosphate (nucleic acids) in the formulations.

They show that the efficacy of cationic orthoester was able to inhibit the expression of RECQL4, whereas the transfecting reagent DOTAU was not able to transfect the siRNA targeting RECQL4.

The invention claimed is:

1. A compound of formula (I),

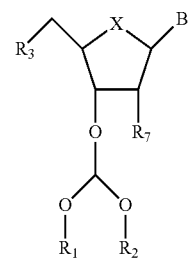

in which
X represents oxygen,
B is thymine,
$R_1$ and $R_2$ are identical and represent a straight or branched $C_2$-$C_{30}$ hydrocarbon chain, which is saturated or partially unsaturated,
$R_3$ is:
  a hydroxy group;
  a $NR_4R_5R_6$ group, in which $R_4$, $R_5$ and $R_6$, identical or different, represent a hydrogen atom, or a $C_1$-$C_6$ straight or branched alkyl chain;
  a phosphate or phosphonate group, which is unsubstituted or substituted by at least one straight or branched, unsubstituted or substituted, $C_1$-$C_6$ alkyl group; a sulfonate group, which is unsubstituted or substituted by at least one straight or branched, unsubstituted or substituted, $C_1$-$C_6$ alkyl group;
  a trialkylamino group;
  a trialkylphoshonium group which is unsubstituted or substituted by at least one straight or branched, unsubstituted or substituted, $C_1$-$C_6$ alkyl group;
  a silyl group, which is unsubstituted or substituted by at least one straight or branched, unsubstituted or substituted, $C_1$-$C_6$ alkyl group;
  a phosphoramidite group, which is unsubstituted or substituted by at least one straight or branched, unsubstituted or substituted, $C_1$-$C_6$ alkyl group,
  or else —O—C(O)—(CH$_2$)$_2$—C(O)—O [(CH$_2$)$_2$—O]$_r$—H in which r is an integer from 4 to 30; and
$R_7$ is hydrogen, a straight or branched, unsubstituted or substituted, $C_1$-$C_6$ alkyl group, a trifluoralkyl, a halogen or a $C_1$-$C_6$ alkoxy group.

2. A compound of formula (I) according to claim 1, wherein in formula (I), in the definitions of $R_1$ or $R_2$, the straight or branched $C_2$-$C_{30}$ hydrocarbon chain is $C_8$-$C_{26}$.

3. A compound of formula (I) according to claim 1, which is selected from the group consisting of:
- ((2R,3S,5R)-3-(bis(hexadecyloxy)methoxy)-5-(5-methyl-2,4-dioxo-3,4-dihydropyrimidin-1(2H)-yl)tetrahydrofuran-2-yl)methyl methanesulfonate,
- 1-((2R,3S,5R)-3-(bis(hexadecyloxy)methoxy)-5-(5-methyl-2,4-dioxo-3,4-dihydropyrimidin-1(2H)-yl)tetrahydrofuran-2-yl)-N,N,N-trimethyl-methanaminium methanesulfonate,
- 1-((2R,4S,5R)-4-(bis(hexadecyloxy)methoxy)-5-(((tert-butyldimethylsilyl)oxy)methyl)tetrahydrofuran-2-yl)-5-methylpyrimidine-2,4(1H,3H)-dione,
- 1-((2R,4S,5R)-4-(bis(hexadecyloxy)methoxy)-5-(hydroxymethyl)-tetrahydrofuran-2-yl)-5-methylpyrimidine-2,4(1H,3H)-dione,
- ((2R, 3S,5R)-3-(bis(hexadecyloxy)methoxy)-5-(5-methyl-2,4-dioxo-3,4-dihydropyrimidin-1(2H)-yl)tetrahydrofuran-2-yl)methyl (2-cyanoethyl) diisopropylphosphoramidite,
- ((2R,3S,5R)-3-(bis(hexadecyloxy)methoxy)-5-(5-methyl-2,4-dioxo-3,4-dihydropyrimidin-1(2H)-yl)tetrahydrofuran-2-yl)methyl methyl phosphate, and
- ((2R,3S,5R)-3-(bis(hexadecyloxy)methoxy)-5-(5-methyl-2,4-dioxo-3,4-dihydropyrimidin-1(2H)-yl)tetrahydrofuran-2-yl)methyl O-Methyl-O'-succinyl-polyethyleneglycol 500.

4. A composition containing at least one compound of formula (I) according to claim 1.

5. A liposome formed from at least one compound of formula (I) according to claim 1, optionally in association with a co-lipid.

6. A complex formed from at least one compound of formula (I) according to claim 1 in association with a co-lipid.

7. A compound of formula (I) according to claim 1, for use as an agent for transportation, vectorization or cellular delivery of at least one therapeutic agent.

8. A pharmaceutical composition containing at least one compound of formula (I) according to claim 1, at least one therapeutic agent and a pharmaceutically acceptable carrier.

9. A pharmaceutical composition according to claim 8, wherein the at least one therapeutic agent is selected from a natural or synthetic molecule used for preventing or treating a pathological condition, or restoring a biological function, in vitro or in vivo, or else in isolated cells.

10. A pharmaceutical composition according to claim 8, wherein the at least one compound of formula (I) is in the form of a supramolecular structure.

11. A compound of formula (I) according to claim 1, wherein $R_3$ is a trimethylamino group.

12. A compound of formula (I) according to claim 1, wherein $R_3$ is —O—C(O)—$(CH_2)_2$—C(O)—O [$(CH_2)_2$—O]$_r$—H in which r is an integer from 10 to 20.

13. A compound of formula (I) according to claim 1, wherein, in the definitions of $R_1$ or $R_2$, the straight or branched $C_2$-$C_{30}$ hydrocarbon chain is $C_{16}$-$C_{20}$.

14. A pharmaceutical composition according to claim 10, wherein said supramolecular structure is a liposome, a micelle or a nanoparticle.

15. A method for the transfecting cells with an siRNA, comprising, forming a complex of the siRNA with a compound in accordance with claim 1, and contacting the cells with said complex.

16. In a method for transportation, vectorization or cellular delivery of least one therapeutic agent comprising transporting, vectorizing or delivering to cells the therapeutic agent in conjunction with a transportation, vectorization or cellular delivery agent, the improvement wherein the transportation, vectorization or cellular delivery agent is a compound in accordance with claim 1.

17. In a method for transportation, vectorization or cellular delivery of least one therapeutic agent comprising transporting, vectorizing or delivering to cells the therapeutic agent in conjunction with a transportation, vectorization or cellular delivery agent, the improvement wherein the transportation, vectorization or cellular delivery agent is a compound in accordance with claim 3.

* * * * *